United States Patent [19]

Summerton et al.

[11] Patent Number: 5,470,974
[45] Date of Patent: Nov. 28, 1995

[54] UNCHARGED POLYNUCLEOTIDE-BINDING POLYMERS

[75] Inventors: James Summerton; Dwight Weller; Eugene Stirchak, all of Corvallis, Oreg.

[73] Assignee: Neu-Gene Development Group, Corvallis, Oreg.

[21] Appl. No.: 202,664

[22] Filed: Feb. 25, 1994

Related U.S. Application Data

[60] Continuation of Ser. No. 880,883, May 8, 1992, abandoned, which is a division of Ser. No. 100,033, Sep. 23, 1987, Pat. No. 5,142,047, which is a continuation-in-part of Ser. No. 712,396, Mar. 15, 1985, abandoned, and a continuation-in-part of Ser. No. 911,258, Sep. 24, 1986, abandoned, and a continuation-in-part of Ser. No. 944,707, Dec. 18, 1986, Pat. No. 5,217,866.

[51] Int. Cl.$^6$ .................... C07D 413/04; C07D 413/12; C07D 473/26
[52] U.S. Cl. .................... 544/118; 544/122; 544/264; 544/335; 549/28; 549/473
[58] Field of Search .................... 544/118, 122, 544/264, 335; 549/28, 473

[56] References Cited

U.S. PATENT DOCUMENTS

| | | | |
|---|---|---|---|
| 3,211,732 | 10/1965 | Schmidt et al. | 544/262 |
| 3,225,042 | 12/1965 | Dillard et al. | 544/262 |
| 3,797,414 | 1/1974 | Yurugi et al. | 544/118 |
| 4,166,105 | 8/1979 | Hirschfield | 544/262 |
| 4,362,531 | 12/1982 | De Steenwinkel et al. | 514/230.8 |
| 4,395,486 | 7/1983 | Wilson et al. | 536/24.5 |
| 4,430,496 | 2/1984 | Abbott | 544/118 |
| 4,469,863 | 9/1984 | Ts'o et al. | 544/262 |
| 4,486,539 | 12/1984 | Ranki et al. | 514/230.8 |
| 4,507,433 | 3/1985 | Miller et al. | 536/24.5 |
| 4,558,047 | 12/1985 | Takaya et al. | 514/230.8 |
| 4,749,647 | 6/1988 | Thomas et al. | 514/230.8 |
| 4,757,055 | 7/1988 | Miller et al. | 536/24.5 |
| 4,775,619 | 7/1991 | Urdea | 435/5 |
| 5,034,506 | 7/1991 | Summerton et al. | 528/391 |
| 5,142,047 | 8/1992 | Summerton et al. | 544/118 |
| 5,217,866 | 6/1993 | Summerton et al. | 435/5 |

FOREIGN PATENT DOCUMENTS

| | | | |
|---|---|---|---|
| 1545860 | 11/1969 | Germany | 548/517 |
| 0172384 | 12/1987 | Japan | 544/118 |
| 9118898 | 6/1990 | Japan | 544/118 |
| WO86/05519 | 9/1986 | WIPO | 544/118 |
| WO86/05518 | 9/1986 | WIPO | 544/118 |
| WO9118898 | 6/1990 | WIPO | 544/118 |

OTHER PUBLICATIONS

Chemical Abstracts, vol. 79, 1973, p. 409, Abstract No. 91870d Poretta et al. "Compounds with anti-blastic activity, etc.".

Khym, J. X., "The Reaction of Methylamine with Peridate–Oxidized Adenosine 5'–Phospate," *Biochemistry* 2: 344 (1963).

Lehninger, *Biochemistry*, Worth Publishers, Inc., p. 130 (1972).

Miller, P. S., et al., "Biochemical and Biological Effects of Nonionic Nucleic Acid Methylphosphonates," *Biochemistry* 20: 1874–1880 (1981).

Miller, P. S., et al., "Oligothymidylate Analogues Having Stereoregular, Alternating Methylphosphonate/Phosphodiester Backbones," *Synthesis and Physical Studies. The Journal of Biological Chemistry* 255: 6959–6965 (1980).

Miller, P. S., et al., "Nonionic Nucleic Acid Analogues. Synthesis and Characterization of Dideoxyribonucleoside Methylphosphonates," *Biochemistry* 18: 5134 (1979).

Murakami, A., et al., "Characterization of Sequence–Specific Oligodeoxyribonucleosides," *Biochemistry* 24: 4041–4046 (1985).

Renz, M., et al., "A Colorimetric Method for DNA Hybridization," *Nucleic Acids Research* 12(8): 3435 (1984).

Serwer, Biosis Abstract No. 57077493, *Journal of Ultrastructure Research* 65(2): 112–118 (1978).

Wu, M., et al., "Transmission Electron Microscopic Method for Gene Mapping on Polytene Chromosomes by in situ Hybridization," *Proc. Natl. Acad. Sci. USA* 78(11): 7059–7063 (1981).

*Primary Examiner*—Mary C. Lee
*Assistant Examiner*—Joseph K. McKane
*Attorney, Agent, or Firm*—Gary R. Fabian; Peter J. Dehlinger

[57] ABSTRACT

A composition of polymer molecules effective to bind, with substantially uniform binding affinity, to a single-stranded polynucleotide containing a target sequence of bases. The polymer molecules are composed of a sequence of base-pairing moieties effective to hydrogen bond to corresponding, complementary bases in the target sequence, under selected binding conditions, and a predominantly uncharged, achiral backbone supporting the base-pairing moieties at positions and in orientations which allow hydrogen bonding between the pairing moieties of the polymer and the corresponding complementary bases in the target sequence. The composition has diagnostic uses, in a solid-support assay system, and therapeutic uses involving inhibition or inactivation of target polynucleotides.

2 Claims, 6 Drawing Sheets

X=F, Cl, Br, I, H, CH$_3$

UNCHARGED POLYNUCLEOTIDE-BINDING POLYMERS

This application is a file-wrapper continuation of U.S. Patent Application Ser. No. 07/880,883, filed May 8, 1992, now abandoned, which is a divisional of U.S. Patent Application Ser. No. 07/100,033, filed Sep. 23, 1987, now issued as U.S. Pat. No. 5,142,047, which is a continuation-in-part application of U.S. Patent Applications Serial Nos. 06/712,396, filed Mar. 15, 1985, now abandoned; 06/911,258, filed Sep., 24, 1986, now abandoned; and 06/944,707, filed Dec. 18, 1986, now issued as U.S. Pat. No. 5,217,866.

1. Field of the Invention

The present invention relates to sequence-specific polynucleotide-binding polymers.

2. References

Balgobin, N., et al., Tetrahedron Lett. 22:3667 (1981).
Blake et al., Biochem. 4:6132 (1985a).
Blake et al., Biochem. 24:6139 (1985b).
Buttrey et al., Tetrahedron 31:73 (1975).
Cassidy et al., Eur. Polymer J. 2:319 (1966).
Cech, D., and A. Holy, Collection of Czechoslov. Chem. Comm. 42:2246 (1977).
Ferruti et al., Recent Advances in Drug Delivery Systems. 1983. Page 69.
Field, M., and H.-P. Rieck, Chemische Berichte. 113:142 (1980).
Fox, J. J., et al., J. Am. Chem. Soc. 80:1669 (1958).
Gait et al., J. Chem. Soc. Perkin Trans. 1:1684 (1973).
Hampton, A., et al., J. Med. Chem. 11:1229 (1968).
Heikkla, J., and J. Chattopadhyaya. Acta Chem. Scand. 837:263 (1983).
Himmelsbach, F., and W. Pfleiderer, Tetrahedron Lett. 24:3583 (1983).
Iwamoto, E. M., et al., J. Med. Chem. 6:684 (1963).
Jayaraman et al., Proc. Natl. Acad. Sci. USA 78:1537 (1981).
Jones et al., Nature 215:505 (1967).
Jones et al., BBA 294:365 ( 1973 ).
Karpova et al., FEBS Letters 122:21 (1980).
Khym, Biochem. 2:344 (1967).
Kohler, P., et al., Nucleic Acid Chemistry (L. B. Townsend and R. S. Tipson, eds.) John Wiley and Sons, Inc. (1976).
Lamaitre et al. Proc. Natl. Acad Sci. USA 84:648 (1987).
Letsinger and Miller, J. Amer. Chem. Soc. 91:3356 (1969).
Miller et al., Biochemistry 18:5134 (1979).
Miller et al., J. Biol. Chem. 255:6959 (1980).
Miller et al., Biochimie 67:769 (1985).
Mertes and Coats, J. Med. Chem. 12:154 (1969).
Mungall and Kaiser, J. Org. Chem. 42:703 (1977).
Murakami et al., Biochemistry 24:4041 (1985).
Niedballa, U., and H. Vorbruggen, J. Org. Chem. 39:3668 (1974).
Pitha, Biochem. Biophys. Acta 204:39 (1970a).
Pitha, Biopolymers 2:965 (1970b).
Reese, C. B., and R. S. Saffhill, J. Chem. Soc. Perkin Trans. 1:2937 (1972).
Robins, M. J., et al., Biochemistry 5:224 (1966).
Smith et al., Proc. Natl. Acad. Sci. USA 83:2787 (1986).
Ti, G. S., et al., J. Am. Chem, Soc. 104:1316 (1982).
Tittensorm, J. Chem. Soc. (C), p. 2656 (1971).
Tullis, Richard, Personal Communication. Molecular Biosystems Inc. San Diego, Calif.
Wallace and Schriesheim, Tetrahedron 21:2271 (1965).
Watanabe & Fox, Angew. Chem. Int. Ed. 5:579 (1966).
Wightman, R., and D. Holy, Collection of Czechoslov. Chem. Comm. 38:1381 (1973).

3. Background of the Invention

Compounds capable of binding specifically to a target single-stranded genetic sequence have many diagnostic and therapeutic applications. For example, in diagnostic applications, the compounds can be used to "hybridize" with analyte single-stranded polynucleotides, to detect with high sensitivity the presence of specific nucleic acid species characteristic of a pathogenic state. In therapeutic applications, the compounds can bind to and inactivate viral genomes, or other single-stranded polynucleotide species characteristic of a pathogenic state. In principle most or all viral diseases and many other diseases may be treatable with suitable sequence-specific gene inactivating agents capable of selectively blocking or reducing the expression in vivo of the offending genes or gene transcripts.

Compounds which are designed to block targeted genetic sequences within living cells can be divided into two general classes:

One class of compounds include sequence-specific nucleic acids, and derivatives thereof, having charged phosphodiester internucleoside linkages. These compounds typically are anti-sense polynucleotide stands designed to bind to and inactivate a target "sense" strand. In spite of the promising work on delivery of modified oligonucleotides into cells in culture (Lamaitre), oligonucleotides coding for or constituting anti-sense nucleic acid sequences probably have little near-term potential for treating vital diseases because of the difficulty in introducing intact nucleic acids into target tissues of the body, principally because nucleic acids (and especially high molecular weight complexes thereof) are rapidly sequestered by the reticuloendothelial system. Even when the nucleic acids are incorporated into liposomes or related delivery vehicles, evasion of the reticuloendothelial cells presents a difficult challenge.

A second class of compounds designed for binding to and blocking target genetic sequences includes nucleic acid analogs with substantially uncharged backbones. Such analogs have the potential for: a) an enhanced rate of passage into living cells (presumably by phase transfer across cell membranes); b) resistance to intracellular enzymatic degradation; and, c) defeating normal cellular mechanisms for strand separating the analog/target duplex. Pioneering work along this line was carried out in the early 1970's (Pitha, 1970b). These workers prepared a variety of homopolymeric polynucleotide analogs in which the normal sugar-phosphate backbone of nucleic acids was replaced by a polyvinyl backbone. The nucleic acid analogs were reported to have the expected Watson/Crick pairing specificities with complementary polynucleotides, but with substantially reduced Tm values (Pitha, 1970a). Subsequently, a variety of other uncharged polynucleotide analogs were reported (Jones, 1967, 1973; Gait; Cassidy; Buttrey).

There are, however, a variety of problems inherent in the structures of uncharged polynucleotide analogs of the type mentioned above. The structures are unstable in aqueous solution; do not allow assembly of different subunits in a defined order; and/or, the base-pairing moieties are not properly spaced for efficient binding to a target sequence. Further, molecular modeling studies carried out in support of the present invention indicate that in some structures the base-pairing moieties are linked too closely to the backbone to allow effective binding of the base-pairing moieties to contiguous bases of a complementary polynucleotide, while in other structures, there are excessive degrees of freedom for the base-pairing moieties, permitting undesired pairing of the moieties with noncomplementary (in the Watson/Crick sense) bases of a polynucleotide.

More recently, uncharged polynucleotide analogs which are nearly isostructural with nucleic acids have been reported. These substances contain chiral intersubunit linkages and include both aryl nitrogen mustard-derivatized (Karpova) and underivatized (Tullis) oligonucleotides having their phosphates in the uncharged triester state. In addition, polynucleotide analogs containing uncharged methylphosphonate linkages between the deoxyribonucleoside subunits have been prepared. These uncharged oligonucleotide analogs have been reported to enter living cells and pair with complementary genetic sequences therein. The methylphosphonate-linked analogs have the further merit of resistance to degradation by nucleases (the phosphotriester-linked analogs appear to be subject to conversion to diesters by an esterase, with subsequent cleavage by nucleases) (Miller, 1979, 1980; Jayaraman; Murakami; Blake, 1985a, 1985b; Smith). Of particular note, the methylphosphonate-linked oligonucleotide analogs have been used successfully to specifically block globin synthesis in rabbit reticulocytes, protein synthesis (N, NS, and G proteins) of Vesicular stomatitis virus in VSV-infected mouse L-cells; T-antigen synthesis in SV40-infected African green monkey kidney cells; and, reproduction of Herpes simplex virus in HSV-infected Vero and human foreskin fibroblast cells.

Despite the potential advantages of uncharged, relatively isostructural oligonucleotide analogs discussed above, the compounds are limited in practical application due to the chiral backbone centers at each methyl phosphonate linkage. Because the methyl moiety on the phosphonate of the internucleoside linkage generates a chiral center, the compounds have atactic (i.e., a random sequence of chiral centers) backbones. Such stereoirregular backbones result in a broad range of analog/target binding constants—the mean of which is substantially reduced in comparison to the binding constant expected for a corresponding stereoregular polynucleotide analog and its complementary polynucleotide. For the methylphosphonate-linked nucleic acid analogs this binding constant reduction and broadening derives from one linkage isomer favoring Watson/Crick pairing of proximal bases and the other linkage isomer inhibiting Watson/Crick pairing of proximal bases. This linkage chirality effect on base-pairing is illustrated in a report which characterizes the two stereo-isomeric forms of a methylphosphonate-linked di(deoxyribonucleoside) (Miller, 1979). The isomeric dimers were coupled via phosphodiester linkages to give partially charged homoisomeric decamers. One such decamer containing the preferred isomeric methylphosphonate linkages paired with its complementary DNA sequence with a Tm of 33° C. In contrast, the corresponding decamer, containing the other isomeric form of methylphosphonate linkages, had a Tm value approximately 30° C. lower (Miller)—suggesting that each linkage having the suboptimal chirality reduces the Tm by about 6° C. Thus, for a methylphosphonate-linked 15-mer, one would predict a given preparation, when paired with its target genetic sequence, would exhibit Tm values over an 84° C. range, with a mean Tm approximately 42° C. lower than for the case of a corresponding specie having all linkages of the preferred chirality.

One feature then of the above-described compounds is that a given preparation will contain multiple molecular species, each with a different target binding constant. Those species having lower binding constants will contribute little or nothing to the target binding activity, while some of those having significantly higher binding constants may also form moderately stable mispaired complexes with nontarget sequences. In therapeutic use, the presence of weak-binding and non-binding components in the preparation can increase the dosage required to achieve a desired therapeutic effect—possibly by as much as two or three orders of magnitude. Further, any significant binding to nontarget sequences by the strongest-binding components increases the possibility of toxic side effects due to inactivation of inherent sequences in the patient.

We have previously described a class of polynucleotide binding polymers having intersubunit linkages which are both uncharged and achiral. U.S. patent applications Ser. No. 712,396, filed 15 March 1985; Ser. No. 911,258, filed 24 September 1986; Ser. No. 944,707, filed 18 December 1986; and PCT patent application Ser. No. US86/00544, filed 14 March 1986. The PCT application is incorporated by reference into the present application. Molecular modeling studies of the compounds, which include carbonate-linked deoxyribonucleosides and carbamate-linked 5'-amino-2',5'-dideoxyribonucleosides, indicate that the component bases in the polymers are properly positioned and spaced for Watson/Crick pairing to complementary genetic sequences. An important advantage of these compounds is that the backbone linkages are achiral, as in natural polynucleotides, and therefore the molecules of the preparation will have uniform binding constants to target single-strand polynucleotides.

In the course of further molecular modeling work, combined with synthesis and target binding studies, several polymers originally described in the above cited patent applications have been identified as preferred structures, either because of better stability, greater ease of synthesis, or improved binding. The present application describes the preferred structures, related polymer structures and synthetic routes for producing the structures.

4. Summary of the Invention

It is therefore one general object of the invention to provide a sequence-specific polynucleotide-binding composition which substantially overcomes problems and limitations associated with prior art polynucleotide-binding agents, and which has been specifically selected for stability, relative ease of manufacture, and binding ability.

Related objects of tile invention include:

(a) Providing such a composition whose polymer molecule components all have substantially the same binding affinity with respect to a-target sequence in a single-stranded polynucleotide;

(b) Providing such a composition which can be designed for targeting against selected genetic sequences within a length range of between about 4–40 base pairs, and which can be prepared in relatively high yield;

(c) Providing such a binding composition having a desired binding affinity for a selected target sequence; and (d) Providing such a binding compound which is suitable for a variety of diagnostic, research, and therapeutic applications.

The invention includes a polymer composition effective to bind to a single-stranded polynucleotide containing a preselected target sequence of bases. The composition is composed of linked-subunit heteromeric polymer molecules having one of the following structures, which show two of the subunits of the structure and an intersubunit linkage:

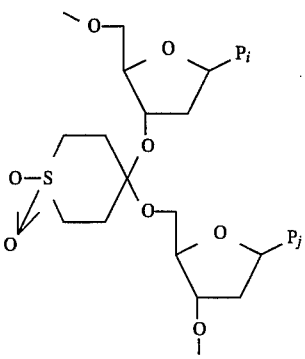
A-A

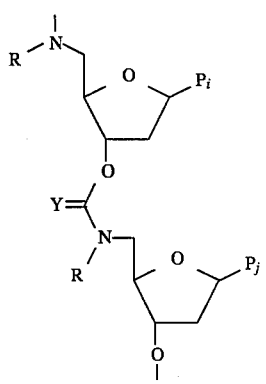
B

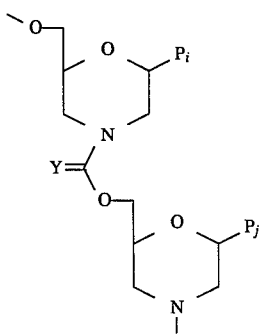
C-C

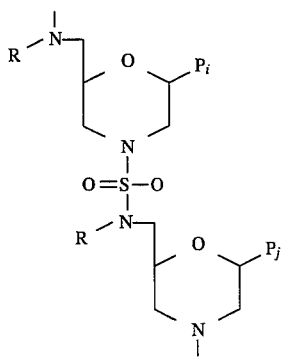
D-D

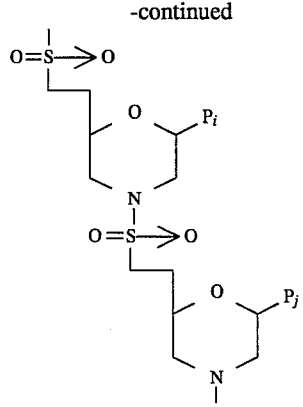
E-E

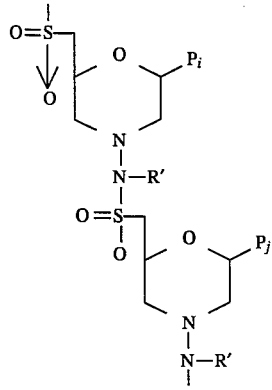
F-F where (i) $P_i$ and $P_j$ are purine or pyrimidine base-pairing moieties, (ii) Y is an oxygen or sulfur atom, and (iii) each R and R' is H, an alkyl, or a substituted alkyl group. The total number and type of base-pairing moieties is such that the polymer molecule can form at least about 12 hydrogen bonds with contiguous, complementary bases of the target sequence. In one preferred embodiment, where R is H, the purine base-pair moieties are selected from purines which do not contain a 2-position amine, or the base-pairing moieties are selected. One preferred polymer structure is the C-C morpholino structure, preferably where Y is an oxygen atom, this polymer being relatively simple and inexpensive to manufacture. Another preferred structure is the B-B carbamate-linked structure having an N alkyl moiety, such as an N methyl group. The polymer may contain one or more solubilizing groups, such as terminal charged groups, or polyethylene glycol for improved solubility in an aqueous medium.

Also included in the invention is a method for producing the polymer composition. This method includes providing a subunit having one of the following structures:

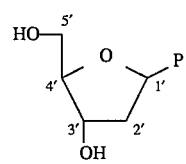
A.

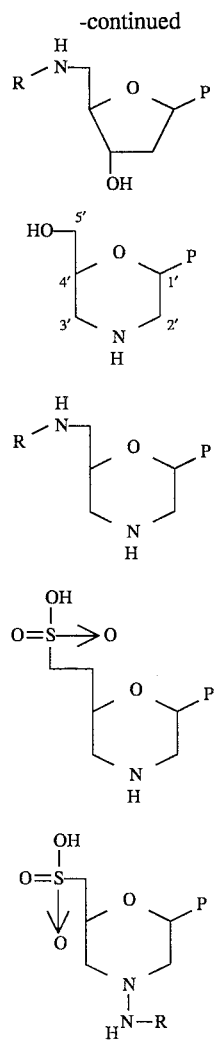

where $P_i$ and $P_j$, and R and R' are as above. These subunits are coupled to form the subunit-linked polymer molecules above, where the total number of base-pairing moieties in the polymer molecules is such that tile moieties are effective to form at least about 12 hydrogen bonds with the complementary bases of the target sequence.

The invention also includes a method for inhibiting the biological activity of a single-stranded polynucleotide. In the method, there is selected a target sequence in the polynucleotide which is required for biological activity. Against this target is constructed a polymer composition of a type described above. The polymer is reacted with the target polynucleotide under conditions which allow base-specific binding of the polymer molecules to the target sequence.

In another aspect, the invention includes subunit C above, which may also be base protected and activated at the 5' hydroxyl group, for subunit coupling, and methods for forming the subunit.

These and other objects and features of the invention will become more fully apparent when the following detailed description of the invention is read in conjunction with the accompanying drawings.

DETAILED DESCRIPTION OF THE INVENTION

Figure 1A:
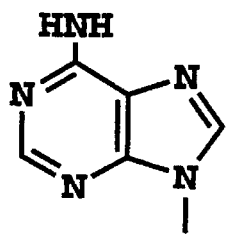
FIGS. 1A to 1J show preferred purine and pyrimidine base-pairing moieties in the polymer molecules of the invention.

The design and selection of suitable polymer subunits and intersubunit linkage types for use in constructing the polymer composition of the invention is described in Section I below. Section II gives details of subunit protective group strategies used in the preparation of the subunits, and Section III, methods of subunit synthesis.

Considerations which are important in the selection of both the target sequence and subunits which will make up the polymer molecules are detailed in Section IV. This section also discusses diagnostic and therapeutic applications of the polymers. Section V details methods of polymer assembly.

I. Subunit Structure and Linkage Selection

A. The Base-Pairing Moiety

Each subunit is composed of a backbone moiety which is linked with other subunit backbone moieties to form the backbone of the polymer, and a base-pairing moiety $P_i$ attached to the backbone moiety. The base-pairing moiety provides two or three hydrogen-bonding groups in a configuration adapted for hydrogen bonding to two or three of the Watson/Crick hydrogen bonding sites on a specified complementary base of the target genetic sequence.

Preferred base-pairing moieties in the invention include the set of purines and pyrimidines shown in FIGS 1(A) to 1(J). The group of subunits used in polymer synthesis includes at least two different base-pairing moieties which are base-specific for different polynucleotide bases, and preferably one or more base-pairing moieties for each of the four bases in a natural DNA or RNA polynucleotide. Also, it is sometimes desirable to provide one group of base-pairing moieties, $P_x$, which are capable of binding with nucleotide bases through two hydrogen bonds, and a second group, $P_y$ which are capable of binding with the same bases through three hydrogen bonds.

The purine structures (FIG. 1) 1(A) and 1(B) are designed to bind to thymine or uracil bases, structures 1(C)–1(F), to guanine bases; structures 1(G)–1(I), to cytosine bases, and structure 1(J), to adenine bases. Structures 1(A), 1(D), 1(E), 1(F), 1(H), and 1(J) are $P_x$ type moieties adapted to bind to complementary bases through two hydrogen bonds, and the remaining structures are $P_y$ type moieties which form three hydrogen bonds on base pairing. As will be seen below, purine and pyrimidine-containing nucleosides are useful in synthesizing a variety of subunits which are suitable for use in polymer synthesis. These nucleosides can be obtained from commercial sources, or prepared according to known methods such as described or referenced in Example 1.

For a binding polymer to have utility as a research tool or as a therapeutic it must bind its target genetic sequence with sufficient avidity as to generate the desired biological effect. Certain genetic sequences are particularly sensitive to such binding (e.g., signal and control sequences and certain ribosomal and transfer RNA sequences). For such sensitive sequences a binding polymer containing as few as four strong-binding base-pairing moieties ($P_y$ type moieties, generating at least 12 hydrogen bonds to the target), are adequate to generate a significant biological effect. However, the vast majority of potential target genetic sequences require more robust binding to achieve a desired biological effect and this generally calls for binding polymers containing on the order of at least 8 base-pairing moieties (generating 16 to 24 hydrogen bonds to the target).

B. The Backbone Moiety

The backbone moiety of each subunit has the general form $N_1$——$N_2$, or $N_1$——E, where $N_1$ and $N_2$ are nucleophilic groups and E is an electrophilic group. The electrophilic group is one capable of reacting directly, or under activating conditions, with $N_1$ to form an E-$N_1$, uncharged achiral backbone linkage between two subunits.

The $N_1$——$N_2$ type subunits are linked by a linking agent capable of reacting with the $N_2$ group of an $N_1$– protected subunit or chain-terminal subunit to form an activated $N_1$——$N_2$-E structure which can then react directly, or after activation, with a second $N_1$——$N_2$ subunit, which may be protected on $N_2$, to form an $N_1$–protected dimer or to effect chain elongation. Based on ease of subunit coupling and required stability of the resultant intersubunit linkage, preferred nucleophilic groups are amino, hydroxyl and hydrazino; and preferred electrophilic groups, and/or electrophilic linking agents, are derivatives of carbonic, thiocarbonic, sulfonic, sulfuric acids, or a derivative of a ketone.

While the total number of possible backbone moiety structures is very large, nevertheless, only a rather limited number of structures are of actual practical value due to a number of factors. As a first condition, only those backbone moieties are considered which contain, or can be readily derived from, deoxyribose or ribose. This limitation is a practical one and reflects the difficulty and corresponding greater expense of de novo synthesized ring structures having multiple chiral centers. Initial screening of promising backbone moieties and intersubunit linkages entailed the use of space-filling CPK molecular models of duplex DNA and RNA, constructed according to parameters determined by x-ray diffraction of oligodeoxyribonucleotides in the B-form and oligoribonucleotides in the A-form. In each of these constructed duplexes, one of the two sugar-phosphate backbones was removed. Next, each prospective backbone was attached, if possible, to the sites on the bases from which the original sugar-phosphate backbone had been removed. Each resulting polynucleotide/polymer duplex was then examined for coplanarity of the Watson/Crick base-pairs, torsional and angle strain in the prospective binding polymer backbone, degree of distortion imposed on the nucleic acid strand, and interstrand and intrastrand nonbonded interactions. Special attention was paid to whether or not amide-containing backbones could readily adopt a conformation in which the amide moieties were planar. This is important because of the substantial energy cost required to force an amide into a nonplanar conformation.

These initial studies confirmed that the optimal unit backbone length (i.e., the $N_1$——E spacing in an $N_1$——E or activated $N_1$——$N_2$-E subunit) is 6 atoms for backbone moieties constituting or derived from deoxyribose or ribose.

Subunit backbone structures judged acceptable in the above modeling studies were then assessed for feasibility of synthesis (on the basis of key synthetic reactions reported in the literature, or reactions carried out on model compounds, and/or via synthesis of the subunits) and stability of the assembled polymer backbone (preliminary stability studies were generally carried out with model compounds or dimers). These types of studies were used to further restrict the number of candidate backbone structures. From this restricted candidate pool the preferred backbone moieties shown in FIG. 2A through 2F were ultimately chosen.

In these figures, subunits containing $N_1$——$N_2$ type backbone moieties include: 2,-deoxyribonucleosides (structure 2A); 2-deoxyribonucleosides substituted at their 5' position with an amino group (structure 2B); and morpholino derivatives of ribonucleosides (structure 2C) which may also be substituted at the 5' with an amine group (structure 2D). Subunits containing $N_1$——E type backbone moieties include: morpholino and N aminorpholino derivatives substituted at their 5' positions with a sulfonic acid (structures 2E and 2F).

C. Linkage Between Backbone and Base-Pairing Moiety

The linkage connecting the backbone moiety to the base-pairing moiety in the polymer subunit must meet certain design criteria which are effective to position the base-pairing moieties for hydrogen bonding to the target polynucleotide bases. In the case of the backbone moieties shown in FIGS. 2A to 2F, modeling studies indicate that the most favorable binding conformation in the polymer occurs when the base-pairing moiety is attached directly to the 1' carbon of the deoxyribose or deoxyribose-derived structures, and to the analogous 1' position of the morpholino structures. That is, the moiety is attached at normal point of attachment and with the normal stereoisomeric configuration of purine or pyrimidine bases to the ribose or deoxyribose groups of nucleosides.

For the preferred backbone moieties, the most favorable binding occurs in nucleosides and nucleoside derivatives having the natural steriosomeric configuration shown in FIGS. 2A to 2F. Subunits of this type can be synthesized, as will be discussed below, using natural nucleoside starting material.

D. Intersubunit Linkage

In addition to the requirement that the intersubunit linkages be uncharged and achiral there are several additional considerations bearing on selection of the intersubunit linkages and polymer structure.

First, if the linkage is such that it exhibits specific rotational conformations (as is the case for amides, thioamides, ureas, thioureas, carbamates, thiocarbamates, hydrazides, thiohydrazides, sulfonamides, sulfamides, and sulfonylhydrazides) then it is important either that the rotational conformation compatible with Watson/Crick pairing be the lowest energy conformation, or that the barrier to rotation between conformations be relatively low (i.e., that the conformations be rapidly interchangeable, at physiological temperatures). Thus a secondary amide (N-alkyl amide), which strongly prefers to adopt a trans conformation would be acceptable if the trans conformation is compatible with Watson/Crick pairing. In contrast, N,N-dialkyl amides (tertiary amides), carbamates, sulfonamides, and related structures generally have two approximately equal low energy conformations and so to be useful in a binding polymer, the linkage types should have a relatively low energy barrier to interconversion between the two conformations. The barrier to rotation between two conformers can be assessed by NMR as follows: At a temperature where the two conformers are interconverting slowly relative to the NMR time scale (on the order of $10^{-8}$ sec) two distinct signals are often seen, each representing a single conformer. As the NMR spectra are taken at progressively higher temperatures, the two conformer signals coalesce—indicating rapid interconversion. The coalescence temperature (Tc) thus provides a useful measure of the rotational freedom of various linkage types. For example, N,N-dimethylformamide exhibits a Tc of about 114° C. (Bassindale) and conformers of analogous tertiary amides have been found to interconvert slowly in biological macromolecules (Nature 279 756 (1979)). By contrast, N,N-dialkyl carbamate (structure 5B, where Y=O and R=$CH_3$) exhibits a Tc of about 44° C. (unpublished results). An N,N-dialkylsulfinamide (which should have a rotational energy barrier similar to that of sulfonamide and related substances) has been reported to have a Tc lower than minus 60° C. (Tet. Let. 10 509 (1964)).

Based on these considerations, backbone linkages containing carbamate, thiocarbamate, sulfonamide, sulfamide, and sulfonylhydrazide linkage types would be preferred over tertiary-type amide, thioamide, urea, thiourea, hydrazide, and thiohydrazide linkages.

Figure 1B:
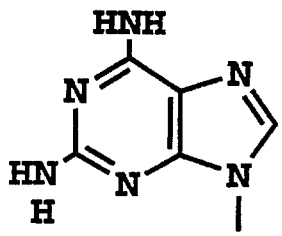
Figure 1C:
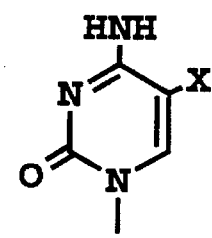
Figure 1D:
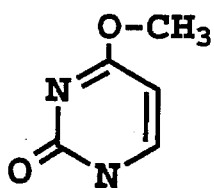
Figure 1E:
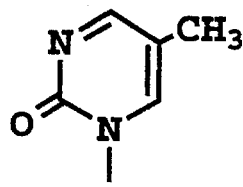
Figure 1F:
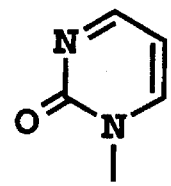
Figure 1G:
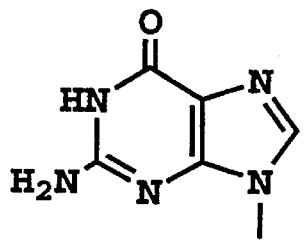
Figure 1H:
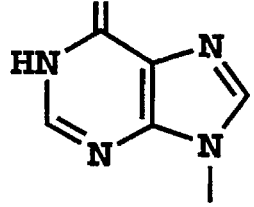
Figure 1I:
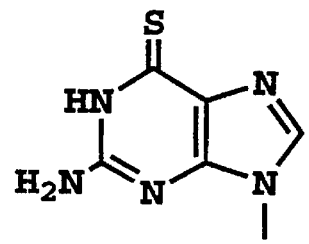
Figure 1J:
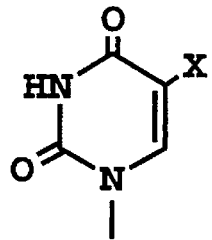

Second, if the linkage can form hydrogen bonds with the NH2 and N3 of a proximal 2-amino-purine-type base-pairing moiety structures shown in FIGS. 1(B), 1(G), and 1(I) positioned in the syn conformation with respect to the glycosidic bond, then binding polymers containing such backbone linkages (e.g., structures shown in FIGS. 5B and 5D) wherein R=H) should not contain such purines. This exclusion of 2-amino type purines can be accomplished simply by using $P_x$ type purines (structures shown in FIGS. 1(A) and 1(H)) instead of $P_y$ type purines (structures shown in FIGS 1(B), 1(G), and 1(I)). Alternatively, if it is undesirable in a given application to incorporate inosine base-pairing moieties (which tend to pair in a non Watson/Crick mode with U and T bases) one can instead select a target sequence lacking C residues.

Third, in regard to ketal type linkages (such as in structure A-A of FIG. 5 and related symmetrical acyclic ketals) a key factor in such linkages is that there be a proximal electron withdrawing moiety (acting through space) which acts to protect the ketal from acid catalyzed hydrolysis. Obviously there are a number of variations of this ketal type linkage, such as the analogous acyclic ketal which contains two sulfone moieties.

II. Protective Group Strategies

Because of the reactivity of the compounds used for activating and/or coupling the subunits, it is generally desirable, and often necessary, to protect the exocyclic ring nitrogens of the base-pairing moieties. Selection of these protective groups is determined by the relative reactivity of the nitrogen to be protected; by the type of reactions involved in subunit synthesis; and by the stability of the completed polymer prior to base deprotection.

Methods for base protecting a number of the more common ribo- and deoxynucleosides from Example 1 are illustrated in Example 2. The methods detailed in the example are generally applicable for forming nucleosides with amine-protective groups. Standard base-protective groups used for nucleic acid chemistry are generally suitable—including benzoyl for the N4 of C; benzoyl or p-nitrobenzoyl for the N6 of A; acetyl, phenylacetyl, or isobutyryl for the N2 of G; and N2,N6-bisisobutyryl for 2,6-diaminopurine residues. These groups can be removed after polymer assembly by treatment with ammonium hydroxide.

It is sometimes desirable to protect the base with a group which can be readily removed by other than a nucleophilic base. Suitable base protective groups removable by a strong nonnucleophilic base via a B-elimination mechanism include: 2-(4-nitrophenyl)ethoxy carbonyl or 2-(phenyl sulfonyl)ethoxycarbonyl for both the N4 of C and the N6 of A; and the 9-fluorenyl methoxycarbonyl for the N2 of G and the N2 and N6 of 2,6-diaminopurine residues. These groups can be removed after polymer assembly by treatment with the strong nonnucleophilic base 1,8-diazabicyclo[5.4.0]undec-7-ene (DBU), under stringently anhydrous conditions.

Temporary protection of a nucleophile of the backbone moiety (for example, N1 in FIGS. 2B to 2F), is preferably achieved using backbone-protective groups which are readily cleaved by mild acid. One primary criterion for selection of protective groups is that they be adequately stable, but not so stable that conditions required for their removal would damage the growing polymer. A particular problem in the case of polymers assembled from backbone moieties derived from deoxyribose is the particular acid sensitivity of the glycosidic bond linking protected purine residues to the C1' of their backbone moieties. The following backbone-protecting groups are preferred: for primary hydroxyls, the di(p-methoxy)trityl group; for primary amines, p-methoxytrityl; and for a secondary amine (as in morpholino-type backbone moieties), trityl. These protective groups can be readily removed by treatment with 0.2 M dichloroacetic acid in dichloromethane.

III. Subunit Synthesis

Figure 2A:
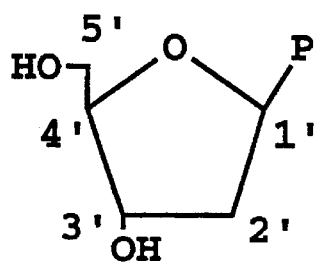
FIGS. 2A to 2F show preferred backbone moieties in the polymer molecules of the invention.

Subunits having a deoxyribonucleoside subunit structure the structure shown in FIG. 2A can be obtained from commercial sources or prepared via literature methods, as described in Example 1. The subunit starting materials include the following ribosides and deoxyribosides, which are identified according to the structure numbers of the recognition moieties given in FIGS. 1(A) through 1(J): adenosine and deoxyadenosine (the structure shown in FIG. 1(A); 2,6-diaminopurine riboside and deoxyriboside (the structure shown in FIG. 1(B); cytidine and deoxycytidine (the structure shown in FIG. 1(C); 4-methoxy-2-pyrimidinone deoxyriboside (the structure shown in FIG. 1(D); 2-hydroxy-5-methyl pyrimidine deoxyriboside (the structure shown in FIG. 1(E); 2-hydroxypyrimidine riboside (the structure shown in FIG. 1(F); guanosine and deoxyguanosine (the structure shown in FIG. 1(G); inosine and deoxyinosine (the structure shown in FIG. 1(H); thioguanosine and deoxythioguanosine (the structure shown in FIG. 1(I); thymidine (the structure shown in FIG. 1(J) where X=$CH_3$); uridine (the structure shown in FIG. 1(J), where X=H;) and 5-halouridines and 5-halodeoxyuridines (the structure shown in FIGS. 1(J), where X=F, Cl, Br or I).

The 5'-amino-2',5'-dideoxyribonucleosides (the structure shown in FIG. 2B where R=H) are prepared according to methods detailed in Example 3. Briefly, the selected deoxyribonucleosides, base-protected if necessary, are reacted with triphenyl phosphine, carbon tetrabromide, and lithium azide to form the corresponding 5'-azidonucleoside, which is then reduced by hydrogenation in the presence of a palladium on carbon catalyst. The nucleosides may be obtained as in Example 1, and base-protected as in Example 2. The stereochemistry of the reactant nucleosides is preserved in forming the 5' amino nucleoside analogs.

An alternative reduction method is used in reducing the azide group of 5'-azido-5-halo uridine, as described in Example 3.2. Here non-catalytic hydrogenation is needed to prevent removal of the ring halogen atom. In forming the 5'-amine guanosine compound, the azide is placed on the 5' position by first tosylating the 5' hydroxyl group, then displacing with azide, as detailed in Example 3.2.

5'-Methylamino-2',5'-dideoxyribonucleosides (the structure shown in FIG. 2B wherein R=$CH_3$) of A, C, G, and T are prepared according to methods detailed in Example 4.

Generally this entails forming the 5' tosylate and displacing with N-benzylmethylamine. Subsequently exocyclic ring nitrogens are protected and then the benzyl moiety removed by catalytic hydrogenation.

An N-methylmorpholino-type derivative of adenosine has been reported (Khym). In that preparation, reduction with sodium borohydride left a hydroxyl on the 3' carbon (numbered as in ribose). It has been found that sodium cyanoborohydride under conditions closer to neutrality gives complete reduction to the desired morpholino product (the structure shown in FIG. 2C).

Figure 2B:
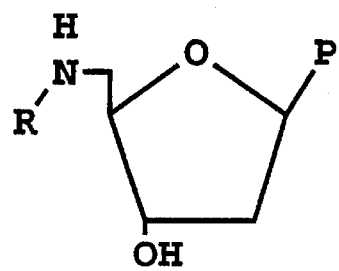
Figure 2C:
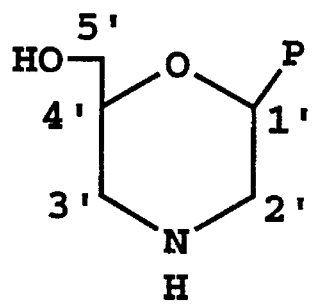
Figure 6A:
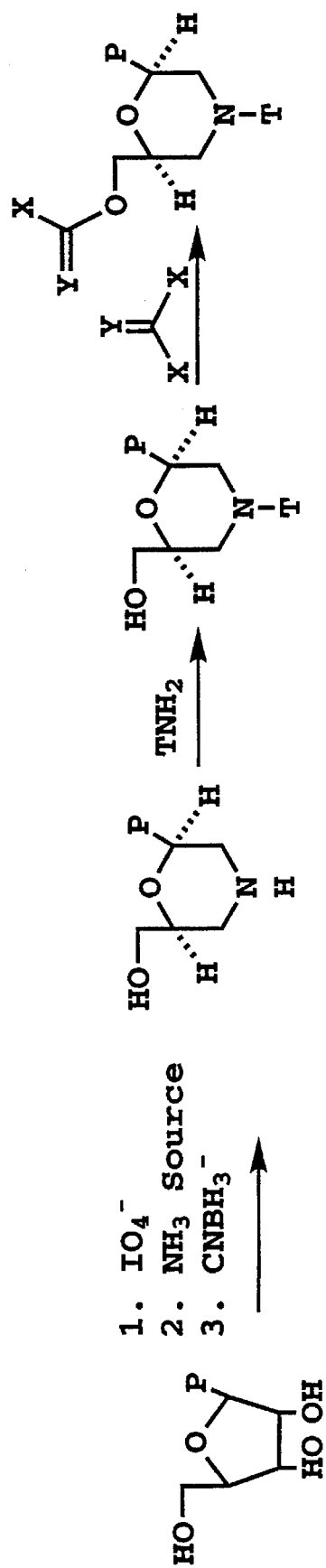
FIGS. 6A and 6B illustrate two general reaction schemes for forming the subunit in FIG. 2C.

Preferred syntheses of the morpholino-type subunit derivatives represented by the structure shown in FIG. 2C are detailed in Example 5. One method which is illustrated in FIG. 6A, entails dissolving a selected nucleoside, base-protected if necessary, in methanol in the presence of an ammonium salt of a weak acid, such as ammonium biborate, and then reacting with sodium periodate to form a transient 2', 3'-dialdehyde, which then closes upon ammonia to form a morpholino ring having 2' and 3' hydroxyl groups. The compound is then treated with sodium cyanoborohydride to reduce the ring hydroxyl groups. The ring nitrogen is preferably protected by trityl derivatization for subsequent subunit coupling. The protective group can be added by reacting the morpholino subunit with a protected primary amine ($TNH_2$), as shown. The stereochemistry of the nucleoside starting material is retained.

In this morpholino synthesis, a variety of other ammonia sources can also be used—including particularly ammonia, ammonium hydroxide, ammonium carbonate, and ammonium bicarbonate. Best results are obtained when the solution is maintained near neutrality during tile oxidation and morpholino ring closure reactions. This can be accomplished by continually titrating the reaction mix or, more conveniently, by using ammonium biborate as the ammonia source. When the solution is too acidic the yield of product is low and when it is too basic side products (possibly due to epimerization at 1' and 4' carbons at the dialdehyde stage) are produced which are difficult to separate from the desired product. It is also noted that the reducing agent can be added before, during, or after the oxidation step with little noticeable effect on product yield.

Ribonucleosides lacking base protection groups can also be successfully oxidized, ring closed, and reduced in aqueous solution. However, in the case of cytidine, and to a lesser extent, for adenosine and guanosine, the number and quantity of undesired side products is greater by this method.

Figure 6B:
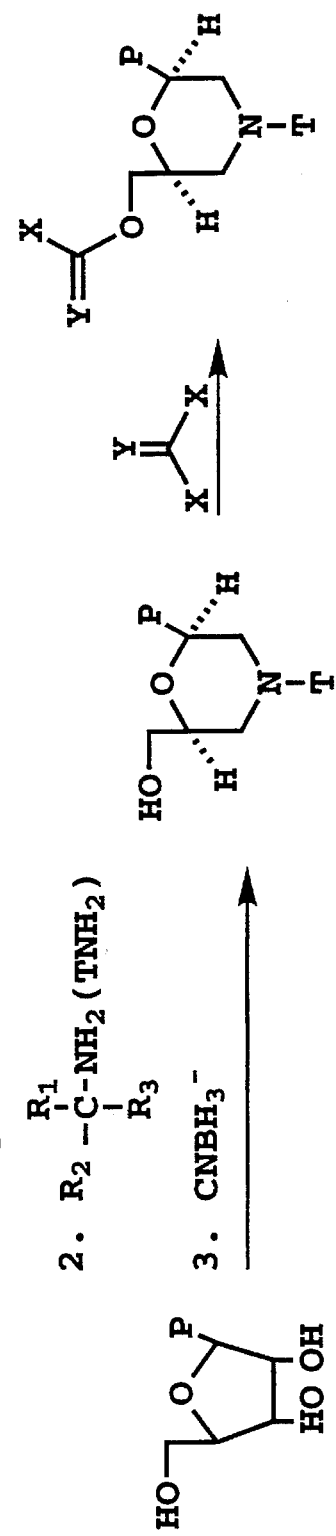

An alternative to the above procedure, illustrated in FIG. 6B, involves dissolving the selected ribonucleoside, base protected if necessary, in methanol in the presence of an arylmethyl amine ($TNH_2$). Sodium periodate and sodium cyanoborohydride are then added. This one-step scheme generates the final subunit (the structure shown in FIG. 2C) with the morpholino nitrogen in the protected state.

FIGS. 6A and 6B also show final activation steps with an activating compound of the type described in section 5A below. The morpholino subunits and their activated forms constitute one aspect of the present invention.

Figure 2D:
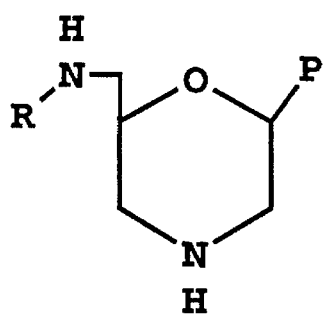

Synthesis of subunits corresponding to the structure shown in FIG. 2D entails a combination of methods used for preparation of the structures shown in FIGS. 2B and 2C, where the morpholino ring is formed and protected first and then the 5' hydroxyl is transformed to an amine.

Figure 2E:
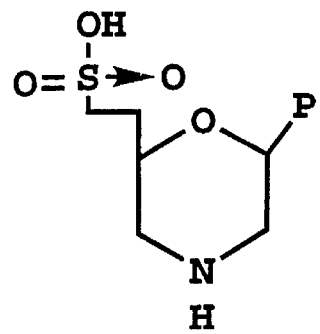

Synthesis of subunits corresponding to the structure shown in FIG. 2E is described in Example 6 and entails oxidizing the 5' OH of N-protected morpholino subunit (the structure shown in FIG. 2C) to an aldehyde. The 5' aldehyde is treated with phenyldiphenylphosphinyl methanesulfonate and then the product is reduced with hydrogen over palladium followed by alcoholic KOH to give the desired product.

Figure 2F:
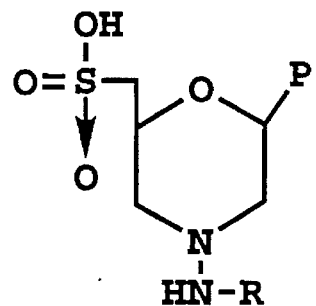

Synthesis of subunits corresponding to the structure shown in FIG. 2F is described in Example 7. This entails conversion of a base-protected ribonucleoside to the 2',3'-isopropylidine ketal. This material is tosylated on the 5' oxygen and then treated with sodium iodide followed by sodium sulfide. The resultant thiol is oxidized to the sulfonic acid. After acid catalyzed cleavage of the ketal the vicinyl diol is oxidized with periodate and closed on a protected hydrazine, followed by reduction with cyanoborohydride to give the desired product.

Activation of subunits corresponding to the structure shown in FIG. 2A and coupling via a ketal linkage is described in Example 8.

IV. Polymer Targeting Considerations

A. Diagnostic Applications

One important application of the uncharged or substantially uncharged polymers of the invention is in a solid-support diagnostic system for use in determining the presence and/or amount of a polynucleotide analyte. The assay system which has been detailed in the above-cited commonly owned U.S. patent applications includes a solid support reagent composed of a solid support and polynucleotide-binding polymers, which are constructed according to the invention linked to a solid support. The polymers are constructed, according to targeting strategies detailed below, for binding specifically to target polynucleotide analyte with a selected melting temperature ($T_m$). The system also includes polycationic reporter molecules which are designed to bind to the fully charged analyte backbone, but not the uncharged or substantially uncharged polymer backbone, under selected binding conditions. Each reporter molecule carries one or more reporter groups, and each polynucleotide can accommodate binding of typically several thousand or more reporter molecules. Thus the system has an amplification factor, in terms of reporter signal per bound analyte molecule, of several orders or magnitude. The assay system and its method of practice are more fully described in co-owned U.S. Patent application for "Polynucleotide Assay Reagent and Method", Ser. No. 712,396, filed Mar. 15, 1985.

The particular merits of using sequence-specific polynucleotide binding polymers having achiral predominantly uncharged intersubunit linkages for diagnostic applications derives from two factors. First, their target binding is relatively insensitive to salt and so the polymer/target annealing step can be carried out under low salt conditions wherein there is no competitive annealing between the target and complementary nucleic acid sequences in the solution. Second, the polymer's reduced charge or uncharged backbone allows use of the above-described reporter molecules which are designed to bind at high density to the target analyte's polyanionic backbone.

The design considerations applied in preparing a polynucleotide binding polymer for use as a diagnostic reagent are governed by the nature of the target analyte and the reaction conditions under which the analyte is to be assayed. As a first consideration, there is selected a non-homopolymeric target base sequence against which the polymer is directed. This target sequence is preferably unique to the analyte being assayed, i.e., is calculated to occur only with some defined small probability (such as 1% or less) in an assay mixture containing a given number of unique-sequence bases. The probability of occurrence of a given n-base target sequence is approximately $\frac{1}{4}^n$— that is, a given n-base target sequence would be expected to occur approximately once in a polymer containing $4^n$ bases. Therefore, the probability P that a given n-base sequence will occur in polynucleotides containing a total of N unique-sequence bases is approximately $P=N/4^n$. To illustrate, the probability P that a 9-base target sequence will be found in a 20 kilobase polynucleotide is about $20 \times 10^3/2 \times 10^5$ or 0.08, the probability that a 16-base target sequence will be present is about $20 \times 10^3/4.3 \times 10^9$ or 0.0000047. From these calculations, it can be seen that a polymer having 9–16 recognition moieties specific for a defined 9–16 base target sequence should ]lave high specificity for the target sequence in an assay mixture containing only viral genomes, whose greatest complexities correspond to about 400K of unique-sequence bases.

Similar types of calculations show that a 12 to 16 subunit polymer can provide adequate specificity for a viral or bacterial target sequence in an assay mixture containing viral and bacterial genomic material only (largest genomic sizes about 5,000 kilobases), and that a 16 to 22 subunit polymer can provide adequate specificity for a target sequence in a polynucleotide mixture containing mammalian genomic DNA material (genomic sizes of about 5 billion base pairs of unique-sequence DNA).

The polymer/analyte binding affinity, and particularly the temperature at which the polymer just binds with the target sequence (the melting temperature, or Tm) can be selectively varied according to (a) polymer length, (b) the number of hydrogen bonds that can be formed between the base-pairing moieties and the corresponding, complementary bases of the analyte target sequence, (c) backbone charge density, and (d) a concentration of denaturants, such as formamide, which reduces the temperature of melting. From a number of studies on model nucleic acid duplexes, it is known that the melting temperature of oligonucleotide duplexes in the 10 to 20 bp range increases roughly 3° C. per additional base pair where the complementary bases are capable of forming two hydrogen bonds, and about 6° C. per additional base pair where the complementary bases are capable of forming three hydrogen bonds. Therefore, the length of a target sequence, which is initially selected to insure high binding specificity with the polymer, may be extended to achieve a desired melting temperature with the complementary-base polymer, under selected assay conditions. Also, where the recognition moieties used in constructing the polymer are the standard nucleic acid bases, as illustrated above, the target sequence may be selected to have a high percentage of guanine plus cytosine bases for achieving a relatively high polymer/analyte melting temperature, or a relatively high percentage of adenine plus thymine bases, for achieving a relatively low melting temperature.

The backbone charge density of the polymer must be substantially less than that of the polynucleotide analyte, to allow preferential binding of polycationic reporter molecules to the analyte, under conditions where reporter binding to the polymer does not occur. This requirement is met where the spacing between the adjacent negative charges in the polymer backbone is at least twice as great as the spacing between adjacent charged phosphodiester linkages in the analyte. The charge density of the backbone also has an important effect on the polymer/analyte melting temperature, particularly under low salt conditions, where any charge-charge repulsion between the analyte and polymer backbones can act to lower the temperature at which the two can anneal. In general, therefore, a polymer having a less-charged backbone would be expected to show (1) a higher analyte/ polymer melting temperature, and (2) less dependence of the melting temperature on salt concentration. Based on these considerations, an uncharged polymer, such as an all-carbamate-linked or all sulfonamide-linked polymer, will allow the analyte/polymer annealing reaction in the diagnostic method to be carried out under a wider range of salt-concentrations than a partially charged polymer, wherein some of the linkages constitute achiral but charged phosphodiester linkages.

B. Therapeutic Applications
Requirement for Adequate Specificity
1. Information Requirements An ideal therapeutic is one which efficiently inactivates a targeted structure unique to the pathogenic state, but which does not detrimentally affect normal structures in the patient. Thus, sequence-specific gene inactivating agents should only effect inactivation of a targeted genetic sequence which contains an amount of sequence information adequate to assure a high probability of that target sequence being unique to the pathogenic state. For example, an agent which can effect target inactivation by binding to only three or four contiguous bases of its target RNA sequence would invariably also attack many mRNAs required for normal cellular functions. In contrast, an agent which requires binding to 30 or more bases in order to effect target inactivation would have an exceedingly small probability of also attacking non-target messengers involved in normal cellular functions.

A reasonable estimation of the desired amount of sequence information which a gene-inactivating agent should recognize when that agent is targeted against a disease-specific mRNA can be calculated as follows. The human genome contains roughly 5 billion base-pairs of unique-sequence DNA. However, essentially all of this material exists in the duplex state and so is largely unavailable for binding to a single-strand-directed polynucleotide-binding agent. Thus, polymer binding is largely restricted to RNA transcripts of the genomic DNA. Of that genomic DNA, something on the order of 1% is transcribed in any given cell type. Further, when all cell types in the patient are considered, it is unlikely that a composite of more than 4% of the entire genome is transcribed in the adult human (i.e., post-embryogenesis). Thus, the sequence complexity of all RNA sequences in the adult human is likely to constitute no more than about 200 million bases—and probably far fewer.

For a gene-inactivating agent to have an expectation of recognizing no target sequences in a cellular pool of 200 million bases of unique sequence genetic material, it should recognize at least n bases in its target, where n is calculated as $2 \times 10^8 = 4^n$—giving a minimal target recognition requirement of 14 bases. This suggests that a gene-inactivating agent recognizing in excess of 14 bases in its target will likely have no targets in cellular pools of normal RNA. Obviously, as the number of bases recognized in the target sequence increases over this value, the probability that the agent will recognize no inherent cellular RNA sequences also increases. It is noteworthy that as the number of bases recognized in the target increases linearly, this "safety factor" increases exponentially. For example, below are tabulated the number of bases recognized in a target sequence and the corresponding expected number of targets in a pool of 200 million bases of unique-sequence single-stranded genetic material:

| No. of bases recognized | Expected no. of targets |
|---|---|
| 12 | 12.0 |
| 14 | .75 |
| 16 | .047 |
| 18 | .0029 |
| 20 | .00018 |

From the above one can conclude that for a sequence-specific gene-inactivating agent destined for therapeutic applications, safety considerations probably mandate that the agent recognize at least 14, and preferably 16 to 20, bases in its target sequence.

2. The Concept of a Minimum Inactivation Length (MIL)

In regard to the amount of sequence information actually "recognized" by a sequence-specific gene-inactivating agent, a useful concept in this regard is that of a minimum inactivating length (MIL), which we define as the minimum number of contiguous bases of a target sequence to which an agent must bind in order to effect gene inactivation in vivo. Irrespective of whether or not the agent binds a longer sequence of bases, it is this MIL value which determines the number of bases in the target "recognized" by that agent—which, in turn, determines the agent's level of sequence specificity.

To illustrate this concept, suppose a gene-inactivating agent has a 16-subunit length but an MIL value of only 10. Such an agent would be expected to inactivate any genetic sequences containing any of the component 10-contiguous-base target sequences. In a cellular pool comprising 200 million bases of unique-sequence single-stranded genetic material, there are an estimated 1000 such target sequences. Further, because the number of base-pairing moieties in the agent is substantially greater than the MIL value, the agent would also be expected to form a variety of partially mispaired complexes with sequences lacking even the required 10-contiguous-base target sequences—with some of those mispaired complexes having sufficient stability to effect inactivation of the participating nontarget genetic sequences.

In contrast, in the case of an agent 16 subunits in length and having an MIL value of 16, by definition, such an agent cannot inactivate nontarget sequences because any partially mispaired complexes with nontarget sequences would not have sufficient stability to effect gene inactivation—only perfect 16-base-pair agent/target duplexes would have adequate stability to effect gene inactivation.

In regard to determining actual MIL values, when a series of gene-inactivation agents, all targeted against the same genetic sequence but varying in number of subunits, are tested in living cells known to contain a functioning single-stranded target sequence, the activity of the targeted gene will show a dramatic reduction at the subunit length corresponding to the MIL value. That is, the MIL value corresponds to that number of subunits just sufficient to block the activity of the targeted genetic sequence.

To illustrate further, below is described an exemplary method for determining the minimum inactivating length for a polynucleotide-binding polymer having any selected backbone linkage type.

First, prepare a regular series of binding polymers having the selected backbone type, targeted against the region 57 to 80 of the rabbit beta-globin in mRNA (5'-GUGCAUCU-GUCCAGTGAGGAGAAG-3'), and ranging in length from 5 to 24 subunits. Next, following the detailed procedures of Blake et al. (1985a), add each of these polymers to a separate portion of a commercial rabbit reticulocyte lysate preparation labeled with [$^{35}$S]-methionine. Thereafter, add rabbit globin mRNA and incubate 1 hour at 37° C. Work each sample up, fractionate by gel electrophoresis, and quantitate the radioactivity incorporated in beta-globin as per Blake et al, above. The minimum inactivating length is that minimum polymer subunit length which effects essentially complete blockage of new beta-globin synthesis.

It should be emphasized that this MIL will vary somewhat depending on the targeted sequence, but in general this relatively simple extracellular method serves to give an approximation of the intracellular MIL for any given backbone type. Once this MIL value has been determined for a selected backbone type, the methods described below for MIL adjustment can be rationally applied for optimizing the MIL for a selected target sequence.

3. Tactics for Adjusting the MIL

It is sometimes necessary to vary an agent's target-binding affinity over a substantial range in order to ultimately achieve an optimal MIL value. To this end, a variety of methods, and combinations thereof, can be used for varying the stability of the agent/target duplex, including:

(i) increasing or decreasing the number of base-pairing moieties in the agent;

(ii) selecting a target having a sequence providing greater or lesser stacking contributions;

(iii) selecting a target sequence containing a greater or lesser proportion of strong-binding bases (G and C) to weak-binding bases (A and U or T);

(iv) replacing one or more weak-binding base-pairing moieties with stronger-binding moieties having the same Watson/Crick pairing specificities (e.g., a 2,6-diaminopurine moiety can be used instead of adenine to effect a substantially stronger bond to U or T in the target sequence; a 5-bromouracil moiety can be used instead of U or T to effect a substantially stronger bond to a in the target sequence; and a 5-bromocytosine moiety can be used instead of cytosine to effect a somewhat stronger bond to G in the target sequence); or replacing one or more strong-binding base-pairing moieties of the agent with a weaker-binding moiety having the same W/C pairing specificities (e.g., a 2-pyrimidinone moiety can be used instead of cytosine to effect a substantially weaker bond to G in the target sequence; and a 6-thioguanine or hypoxanthine moiety can be used instead of guanine to effect a substantially weaker bond to C in the target sequence); and (v) selecting a backbone structure so as to somewhat inhibit or enhance Watson/Crick pairing to the target sequence.

It should be noted that the first three of the above methods actually comprise target selection procedures, while the latter two methods are effected during synthesis of the agents.

A difficulty with method (i) is that sequence specificity requirement generally preclude reduction of the agent's length to less than about 14 subunits. The difficulty with methods (ii) and (iii) is that other more critical targeting criteria can so limit the optimal target region that these two MIL adjustment methods have little latitude in which to achieve a significant effect. Because of these limitations MIL adjustments are often best achieved by methods (iv) and (v).

V. Polymer Assembly

The coupling reactions used in forming the polymer molecules of the invention are stepwise reactions which join one selected subunit or subunit sequence to another selected subunit or subunit sequence. For purposes of the present discussion, the coupling reactions will be described generally with respect to coupling a single subunit having a selected base-pairing moiety $P_1$ to another single subunit having the same or a different selected base-pairing moiety $P_2$, to form a dimer having the base-pair moiety sequence $P_1$-$P_2$.

A. Subunit Coupling: $N_1$—$N_2$ Backbone Types

General methods for coupling subunits having an $N_1$—$N_2$ backbone type are illustrated in FIG. 3. As indicated in Section III above, $N_1$ and $N_2$ are nucleophilic backbone groups, such as hydroxyl and amine groups, which can be activated with an electrophile E, to form an activated $N_1$-E or $N_2$-E backbone group which can then react with a second $N_1$—$N_2$ type backbone moiety to form an $N_1$—$N_2$-E-$N_1$—$N_2$ backbone-linked dimer. The subunit backbones of these types which have been described specifically above are the backbone the structures shown in FIGS. 2A through 2D. In the structures shown in FIGS. 2A and 2B, the activated $N_2$ nucleophile is the 3' hydroxyl group; in the structure shown in FIG. 2C, is the 5' hydroxyl; and in the structure shown in FIG. 2D, the 5' amino.

Figure 3A:
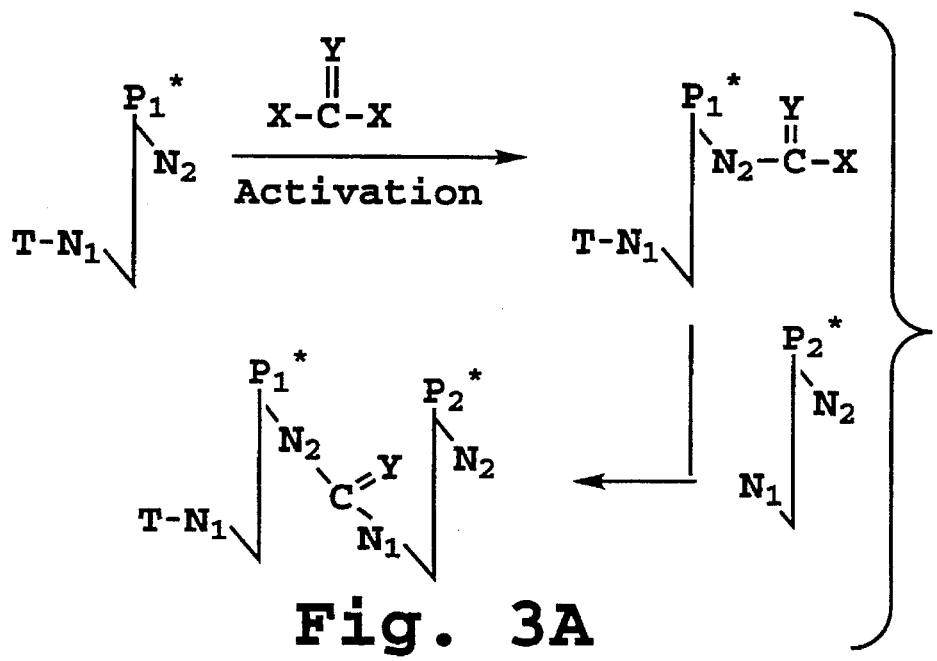
FIGS. 3A and 3B illustrate two preferred subunit assembly schemes for coupling $N_1$—$N_2$ type polymer subunits.

In a preferred coupling method, which is illustrated in FIG. 3A, a subunit having a selected base-pairing moiety $P_1$ is activated with an electrophile E. The star at the pairing moiety indicates any required base protection. As seen in the figure, the selected subunit is protected (T) at its $N_1$ nucleophile, to ensure that (a) only the $N_2$ nucleophile is activated and (b) the activated subunit cannot self-polymerize. In the structure shown in FIG. 2A, in which the backbone protective group is on the 5' hydroxyl, the protective group is preferably the acid-labile group, dimethoxytrityl (DMTO). In the structure shown in FIG. 2B wherein R=H the protective group is preferably methoxytrityl; and in the structures shown in FIGS. 2C and 2D the protective group is preferably trityl.

The activating reagent shown in FIG. 3A has the general form:

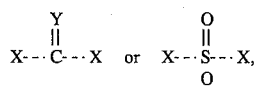

where Y is oxygen or sulfur, and X is a good leaving group such as p-nitrophenol, 2-4-denitrophenol, imidazole, or triazole and the two X's may, but need not, be the same.

Activating agents, such as bis-p-nitrophenyl carbonate, which give the carbonyl activated subunit (Y=O), are used in forming carbamate intersubunit linkages. Similarly, activating agent, such as thiocarbonyl-di-(1,2,4-triazole) (Y=S) are used in forming thiocarbamate linkages. Activating agents such as sulfonyl-ditriazole are used in forming the sulfamide linkage.

Subunit activation reactions involving carbonyl activated subunits are detailed in Example 9 and reactions involving sulfonyl activated subunits are described in Example 10. The general reaction conditions used to activate the nucleophilic groups in these structures are broadly applicable.

Following the activation reaction, the activated complex is purified by conventional methods, such as silica gel chromatography, and then reacted with a second subunit whose selected base-pairing moiety $P_2$ will form the next in-sequence base-pairing moiety in the completed polymer. The coupling reaction is preferably carried out under mild conditions in which the activated group can react with backbone $N_2$ amine groups, but not $N_1$ hydroxyl groups. Therefore, the method is suitable for coupling subunits of the type represented by the structures shown in FIGS. 2B and 2C, but not the structure shown in FIG. 2D. An advantage of this coupling method is that the second subunit—which contains an amine $N_1$ nucleophile and a hydroxyl $N_2$ nucleophile—will be coupled to the first activated subunit only through the $N_1$ amine, so it is not necessary to protect the $N_2$ backbone group. The resulting dimer subunits are therefore coupled through an $N_2$—E—$N_1$ linkage, as indicated in the figure.

The oligomer can be extended by repeating the above steps of (a) activating the free $N_2$ nucleophile in the second subunit, separating the activated species from the activating agent, and coupling the activated compound with the next-in-sequence subunit, whose backbone is unprotected. This method is used particularly in forming short oligomer blocks by solution methods which will be described below and which are suitable for solid-phase block assembly.

Figure 3B:
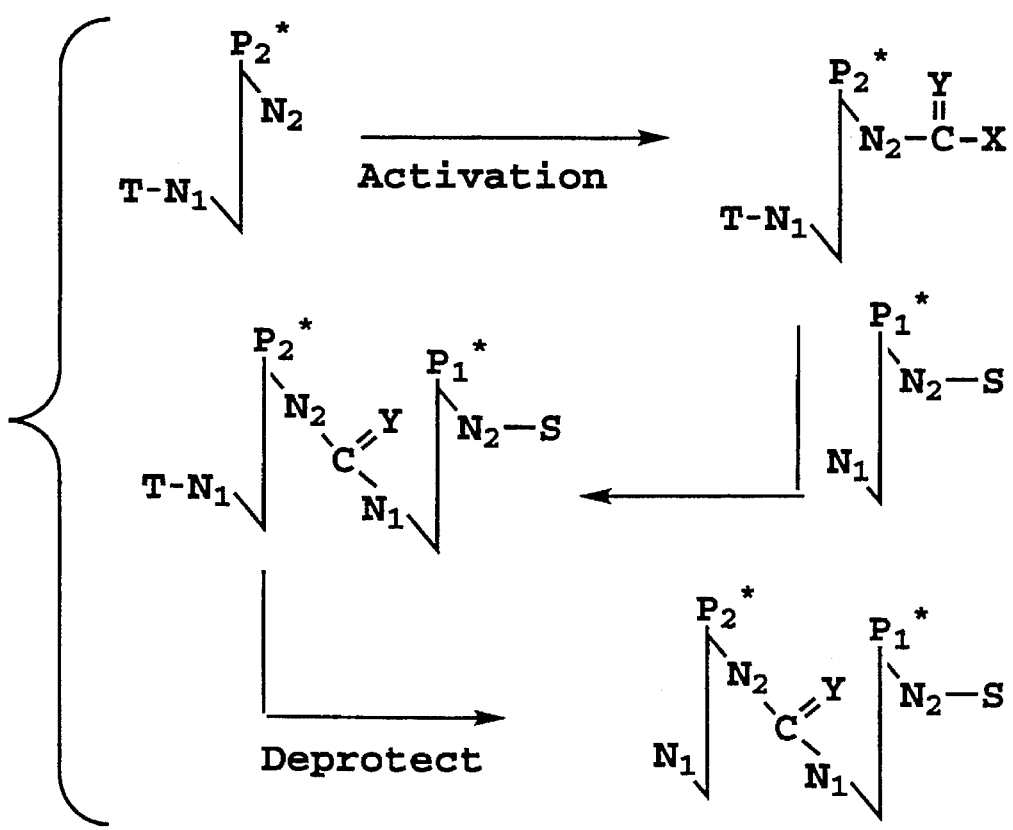

For forming a polymer by solid-phase sequential subunit or block addition, the coupling method outlined in FIG. 3B is preferred. The second method differs from the method illustrated in FIG. 3A in that polymer growth occurs by addition of an excess of activated subunit to an existing protected subunit or oligomer, rather than, as in the first method, by addition of a nonactivated/nonbackbone protected subunit or oligomer to an activated subunit or chain. In FIG. 3B, the existing subunit or subunit chain is shown by a subunit whose base-pairing moiety is $P_1$ (second line in FIG. 3B). This subunit has a free $N_1$ backbone nucleophile and an $N_2$ nucleophile which is protected by a preferably acid-stable linkage to a solid support or by virtue of being linked to a chain of subunits which are linked to a solid support. A method for forming subunits which are $N_2$ protected in this manner are described generally in Example 13. The terminal subunit (the most recently added subunit in a growing polymer) is now reacted with an activated subunit which thereby becomes the next-in-sequence subunit in the polymer. This activated subunit, which is activated at its $N_2$ backbone site, and protected at its $N_1$ site, preferably by an acid-labile protective group, is prepared by methods described above with reference to FIG. 3B.

As seen in FIG. 3B, the coupling reaction adds the $N_2$-activated second subunit to the $N_1$-protected first subunit to couple the two through an $N_2$-E-$N_1$ linkage, and form a compound which is protected at both free backbone nucleophile sites. This compound is now treated, for example by reaction with acid, to deprotect the acid-labile $N_1$ protective group on last-added subunit, and the procedure is repeated to build up a desired sequence polymer.

It can be appreciated from the above that the $N_2$-activated subunit which will form the last-in-sequence subunit must be protected at its $N_1$ backbone site, to allow selective activation at the $N_2$ site and to prevent self-polymerization of the activated compound. Also the $N_1$-deprotected subunit which is to couple to the activated subunit should be protected at its $N_2$ site to allow selective reaction of its $N_1$ moiety with the $N_2$-activated subunit. Therefore, since the reacting subunits are both protected at one backbone site, the method is suitable for coupling subunits whose backbone moieties contain both amine and hydroxyl backbone nucleophiles and for coupling subunits wherein both nucleophiles are amines, such as the structures shown in FIGS. 2B through 2D.

The advantage of the coupling method illustrated in FIG. 3B is that a substantial molar excess of the activated subunit can be added to the growing support-bound polymer at each polymer-addition step, to achieve subunit coupling to a very high percentage of the support-bound polymers. This insures that a large percentage of the support-bound polymers will contain the complete sequence of subunits desired. In contrast, in the first method, where the growing polymer is activated at its last-added subunit, the efficiency of subunit addition is limited by the efficiency of the activation steps.

The method used in coupling the subunit structures shown in FIG. 2A through a ketal linkage are detailed in Example 12. Briefly, a subunit containing a 5' protected backbone moiety is activated at its 3' hydroxyl, and reacted with another subunit (or growing chain) which is protected at its 3' hydroxyl.

Figure 5C:
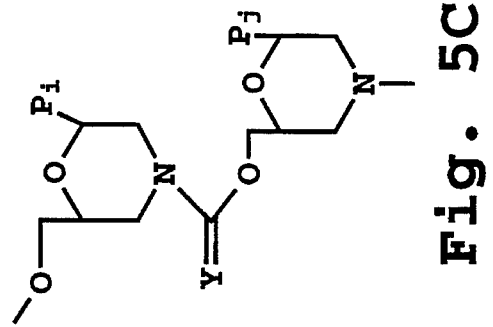
FIGS. 5A to 5F show the linked subunit structures formed by linking $N_1$—$N_2$ type subunits (subunits in FIGS. 2A–2D) and $N_1$—E type subunits (subunits in FIGS. 2E and 2F)
Figure 5B:
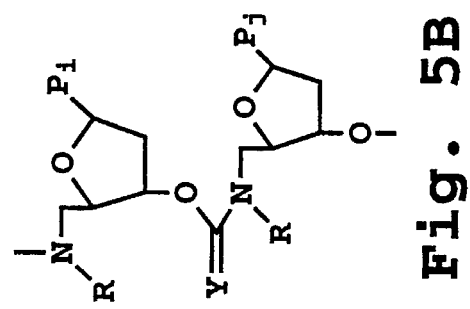
Figure 5A:
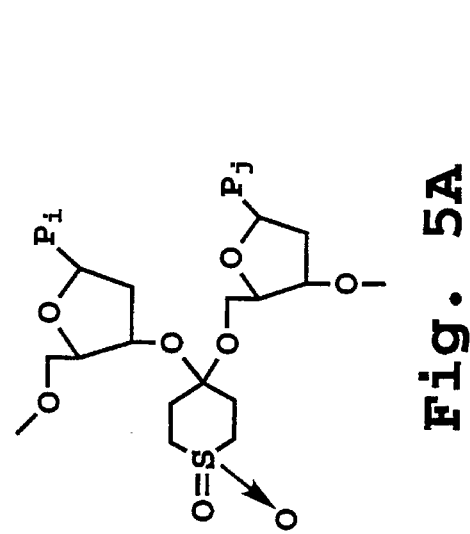
Figure 5F:
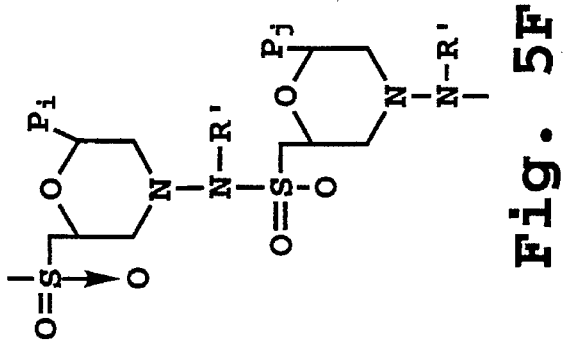
Figure 5E:
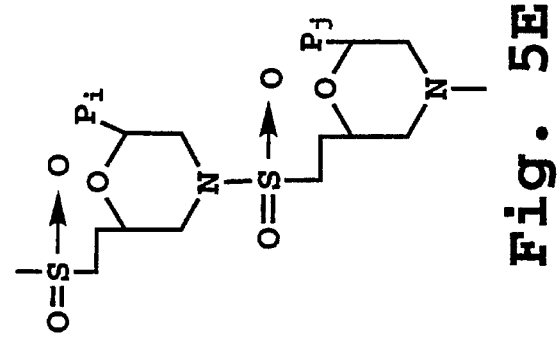
Figure 5D:
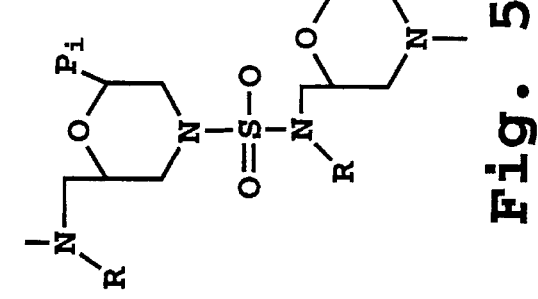

FIGS. 5A through 5D show the dimeric structures produced by coupling the backbone moieties of the structures shown in FIGS. 2A–2D. The nucleoside subunits in the structure shown in FIG. 5A are joined by a stabilized ketal linkage. The structures shown in FIGS. 5B and 5C are joined by a carbamate (Y=O) or thiocarbamate (Y=S) linkage; the structure shown in FIG. 5D is joined by a sulfamide linkage. As seen from the figure, all of the illustrated subunit linkages are uncharged and achiral, i.e., do not contain chiral centers. In addition, the linkages are stable in aqueous medium, as judged by the ability of polymers to resist hydrolysis over an extended period in neutral aqueous solution.

According to another important feature of the invention, the structures, when joined to form polymers, can undergo Watson/Crick base pairing with complementary polynucleotides.

B. Subunit Coupling: $N_1$—E Backbone Types

Figure 4A:
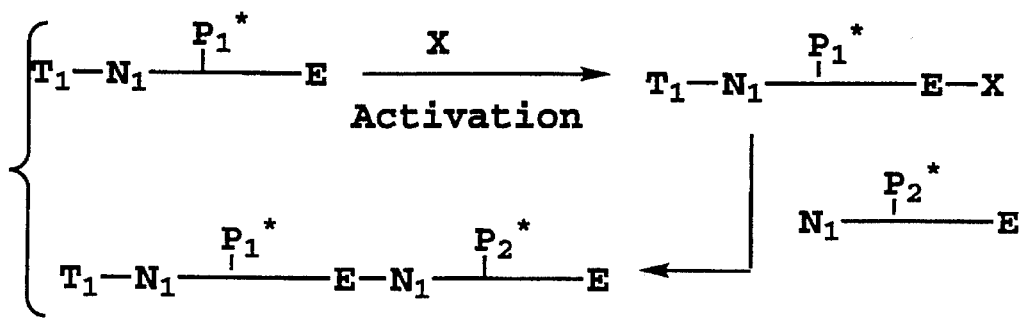
FIGS. 4A–4C illustrate three preferred subunit assembly schemes for coupling $N_1$—E type polymer subunits.
Figure 4B:
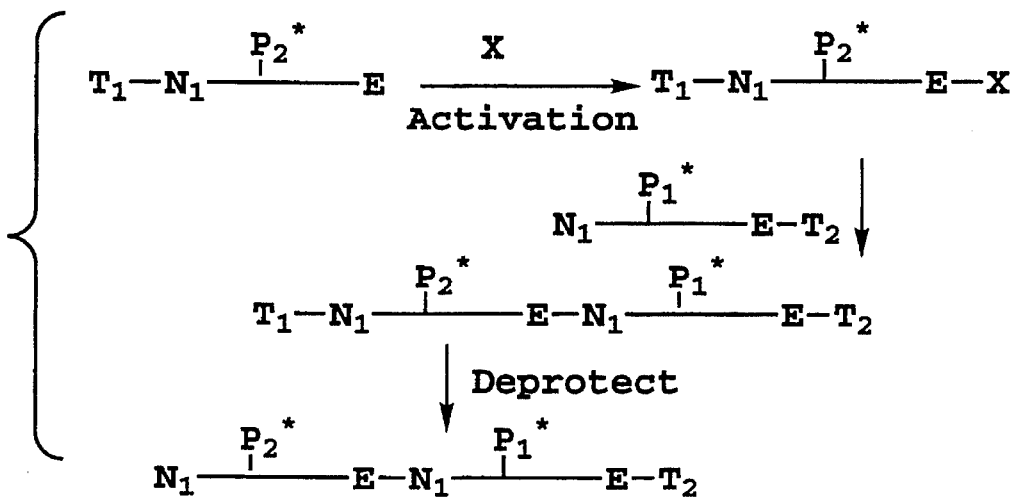
Figure 4C:
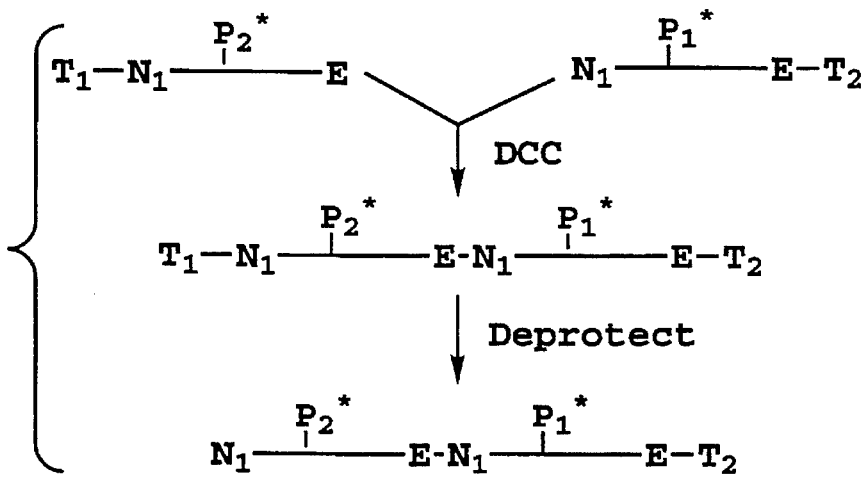

General methods for coupling subunits having an $N_1$—E backbone configuration are illustrated in FIGS. 4A, 4B, and 4C. The subunit backbone moieties of this type which have been described specifically above are the backbone structures shown in FIGS. 2E and 2F. In the structure shown in FIG. 2E the $N_1$ nucleophile is the morpholino nitrogen and in the structure shown in FIG. 2F the $N_1$ nucleophile is the hydrazino moiety.

The first coupling method, which is illustrated in FIG. 4A, is analogous to the method described above with reference to FIG. 3A, where a first $N_1$-protected subunit is activated, then coupled directly to a backbone-unprotected subunit which forms the next-in-sequence subunit in the growing polymer. The protective group $T_1$ on the subunit $N_1$ is preferably an acid-labile protective group, such as trityl. Methods for $N_1$-protecting backbone structures are analogous to procedures described above for the structures shown in FIGS. 2A through 2D.

The activation reaction is designed to yield an activated or chain-terminal moiety of the form $N_1$—E—X, where X is a good leaving group, and the activated subunit has much the same reactivity toward backbone nucleophilic groups as does the activated subunit in the previously described method. That is, the activation is designed to produce the same active coupling group as in the $N_1$—$N_2$ type backbones, but where the reactive sulfonyl group is provided by the backbone itself rather than by a carbonyl or sulfonyl activating reagent, as in the methods shown in FIG. 3.

The activation can be performed readily by reacting the $N_1$-protected $N_1$—E type subunit with a carbodiimide followed by addition of 1,2,4 triazole. Such subunit activation reactions are detailed in Example 11.

Following the activation reaction, the activated complex is purified by conventional methods, such as silica chromatography. The coupling reaction yields a dimer whose subunits are coupled through an E—$N_1$ bond, as indicated in the figure. As above, subunits must be suitably base protected during the activation reaction.

The polymer can be extended by repeating the above steps of (a) activating the free E electrophile in one subunit, (b) separating the activated species from the activating agent, and (c) coupling the activated compound with the next-in-sequence subunit, whose backbone $N_1$ is unprotected.

A second coupling method, which is illustrated in FIG. 4B, is directly analogous to the method described above with respect to FIG. 3B. Here a first subunit having an E-protected backbone (the protecting groups is indicated at $T_2$) is reacted with a second subunit with an activated E group and a protected $N_1$ nucleophile, to form a dimer linked through an E—$N_1$ bond and protected at both free backbone end groups. Where the polymer is being formed by solid-phase synthesis, the $P_2$ protective group $T_2$ preferably takes the form of an acid-stable linkage to a solid support. The $N_1$-protected subunit is prepared and activated as above. Coupling conditions generally follow those used in the above subunit coupling reactions.

In the third coupling method, shown at FIG. 4C, the $N_1$-protected and E-protected subunits (or oligomers) are reacted together in the presence of a suitable E-activating agent, such as a carbodiimide, as indicated FIGS. 5E and 5F shows the dimeric structures produced by coupling the backbone moieties shown in FIGS. 2E and 2F, respectively. The nucleoside subunits in the structure shown in FIG. 5E are joined by a sulfonamide linkage and in the structure shown in FIG. 5F the subunits are joined through a sulfonyl hydrazide linkage. Like the above-discussed dimer structures, these subunit linkages are uncharged and achiral, and stable in aqueous medium.

All of the structures shown in FIGS. 5A through 5F have the additional requisite property that the corresponding polymer molecules are effective to bind single-strand RNA or DNA by sequence-specific base pairing with a target sequence.

C. Polymer Assembly Strategies i. Geometric Assembly

After selecting a desired polymer length and recognition moiety sequence, according to factors considered in Section IV, the polymer is assembled, using the general subunit coupling procedures detailed above. One method of polymer assembly involves initial preparation of an appropriate set of dimers, linking selected dimers to form tetramers, linking these to form octamers, and so on. This method is carried out in solution, substantially according to methods described with reference to FIGS. 3A, 3B and FIGS. 4A, 4B and 4C above. It should be noted that couplings need not involve oligomers of equal size. For example, often it is desirable in the last coupling to link a hexadecamer with a tetramer to give a 20-mer or to link a 16-mer with an octomer to give a 24-mer.

A particular merit of this assembly method is that each coupling product is roughly twice the mass of the precursors and so purification of the product of each coupling is simplified. Example 12 details the assembly of an 8-subunit polymer formed by this method and describes methods for configuring the polymers for specific applications, as well as the procedure for final deprotection of the bases. Purification of the completed polymer is described in Example 14.

ii. Stepwise Assembly on a Solid Support

Another preferred method for polymer synthesis is stepwise assembly on a solid support. Here the first subunit or oligomer of the polymer is attached through its E backbone function to a solid support. Typically, a solid support, such as glass beads derivatized with acid-stable, long-chain linkers, are employed as the support material, and prepared for attachment of the first subunit, as described in Example 13. The glass beads are reacted with a subunit which has a preferably acid-labile $N_1$ protected group, and an activated base-labile $N_2$ or E backbone group or activated extension thereof. The coupling of various types of subunits to a glass-bead support is also described generally in Example 13.

After coupling the second subunit (or oligomer which may be assembled in solution) to the support, any unreacted nucleophilic sites can be capped by addition of a suitable capping reagent, such as p-nitrophenyl acetate or acetic anhydride, and thereafter the support is washed. The protecting group on the $N_1$ terminal subunit is removed, typically by acid treatment, and after neutralization, the support is then reacted with an excess of the next-in-sequence subunit (or polymer unit) which is activated at its free $N_2$ or E backbone moiety. The excess of activated component maximizes the number of support-bound chains which are chain-elongated. That is, one feature of the solid support assembly method is the need for high coupling efficiencies at each subunit addition step, and the concentration of added activated subunit is selected to maximize this efficiency. Chain elongation is continued in this manner, with optional capping of failure sequence, after each subunit addition, until the polymer of the desired length and sequence is achieved. The general method is illustrated in Example 13.

After addition of the final subunit, the terminal backbone $N_1$ may be reacted with a suitable charged or uncharged substance, as described in Examples 12 and 13. After derivatizing the terminus (if desired), the polymer is cleaved from the support, e.g., by treatment with ammonium hydroxide, and the bases deprotected as further described in Example 13. Thereafter the finished polymer is purified as described in Example 14.

D. Configuring the Polymer for Specific Applications

When the binding polymers are to be used for inactivating target genetic sequences within cells, it is generally necessary that they exhibit a reasonable solubility in aqueous solution. In neutral aqueous solution some of the longer binding polymers disclosed herein have solubilities only in the sub-micromolar range. Therefore, it is generally desirable to substantially increase that solubility. We find that this can be readily accomplished by methods modeled after those of Ferruti et al. As detailed in Examples 12 and 13, for most of the polymer types disclosed herein this can be accomplished by cleaving the terminal backbone protective group from the completed binding polymer. This polymer, with the bases still in the protected state, is next reacted with a substantial excess of carbonyldiimidazole-activated polyethylene glycol (PEG). Thereafter the binding polymer is treated with ammonium hydroxide to remove the base-protected groups and then purified in the standard manner. The level of solubilization is easily adjusted through proper selection of the PEG material. Suitable PEG fractions having average molecular weights of 200, 400, 600, 1,000, 1,540, 3,400, 4,000, 6,000, 7,500, and 18,500 daltons are commercially available from Polysciences, Inc.

For some applications it is desirable to have the solubilizing moiety readily clearable from the binding polymer in a biological system. This can be achieved by interposing between the PEG moiety and the binding polymer a natural oligopeptide (cleavable by peptidases). This entails protecting hexaglycine (Sigma Chemical Co.), or a related oligopeptide, with methoxytrityl and then coupling it using dicyclohexylcarbodiimide (DCC) to an N-terminal amino moiety of a binding polymer having its bases still in the protected state. The methoxytrityl is then removed from the peptide terminus with acid and the desired PEG coupled to the N-terminus of the polymer-bound oligopeptide, as described above.

It may also be desirable to modify the polymer so as to favor its cellular uptake via endocytosis. This can be accomplished by cleaving the terminal N-protective group from a binding polymer having protected bases, and treating said polymer with an excess of bifunctional crosslinking agent, such as those available from Pierce Chemical Company and particularly disuccinimidyl suberate. The derivatized polymer is then added to polylysine (or other biologically labile polyionic substance), yielding a high molecular weight water-soluble complex which can preferentially enter cells by an endocytosis mechanism.

Where the polymer molecules are to be attached to a solid support, for use in a diagnostic systems the terminal N-protective group can be cleaved (leaving the bases still in the protected state) and reacted with a suitable crosslinking agent, such as disuccinimidyl suberate. This preparation is then added to the support material, such as latex microparticles containing suitable linker arms terminating in primary amine moieties. Alternatively, if it is desirable to rigorously purify the binding polymer prior to attachment to the support then a methoxytrityl-protected 6-aminocaproic acid can be linked to the unprotected N-terminus of the binding polymer using DCC. The binding polymer is then treated with ammonium hydroxide to deprotect the bases, purified by standard methods, and then the terminal methoxytrityl cleaved from the aminocaproic acid moiety. Finally, the purified polymer is mixed with support material having suitable linker arms terminating in p-nitrophenylester moieties, to give covalent coupling of the polymer molecules to the support.

E. Polymer Deprotection

Binding polymers assembled in solution (Example 12) are typically base-deprotected by suspending in DMSO and carefully layering on an equal volume of concentrated ammonium hydroxide. After tightly capping, the preparation is mixed with shaking and incubated at 30° C. for 16 hrs. Workup includes removing the ammonia under reduced pressure. If a protective group (generally trityl or a related acid-labile moiety) is present, this group is cleaved and the crude polymer preparation is suspended in the buffer to be used for purification, as will be described in a following section.

Binding polymers assembled by a solid-phase method (Example 13) can be cleaved from the support by volume of con $NH_4OH$, capping tightly, and slowly agitating suspending the dried support in DMSO, layering on an equal for 16 hrs at 30° C. The solid support material is removed by filtration and the filtrate is treated as described above.

F. Polymer Purification

At pH 2.5 cytosine and adenine moieties carry a positive charge and guanine carries a partial positive charge. At pH 11 guanine, thymine, uracil and hypoxanthine carry a negative charge. These pH-dependent ionizations can be used for purification of the polymer molecules by ion exchange chromatography. For polymers in which about 50% or more of the base-pairing moieties are ionized at pH 2.5, the purification can be carried out by cation exchange on a column of S-Sepharose fast-flow (Pharmacia) developed with a shallow NaCl gradient buffered at pH 2.5. The effluent is monitored at 254 nm and collected in a fraction collector. The full-length polymer, which elutes after the shorter failure sequences, can be further purified and desalted on a column of chromatographic grade polypropylene (Polysciences Inc.), eluted with an aqueous gradient of acetonitrile adjusted to pH 2.5 with formic acid, with the eluant being monitored at 254 nm. The fractions containing the pure product are neutralized and/or dried under reduced pressure.

For polymers in which about 50% or more of the base-pairing moieties are ionized at pH 11, the purification may be performed on an anion exchange column of Q-Sepharose fast-flow (Pharmacia) developed with an aqueous pH 11 gradient of NaCl. The full-length polymer, which elutes after shorter failure sequences, is further purified and desalted on a polypropylene column eluted with an aqueous pH 11 gradient of acetonitrile. Fractions containing the pure product are neutralized and/or dried.

The purification methods described above should be carried out so that deoxyribose or deoxyribose-derived polymers (the structures shown in FIGS. 2A and 2B) are not exposed to pH 2.5 for more than a few hours at room temperature, and so that polymers containing adenine base-pairing moieties are not exposed to pH 11 for more than a few hours at room temperature, to avoid potential acid or base lability problems.

G. Structural Characterization

Fully-protected binding polymers of moderate size (10 to 16 subunits) often give a strong molecular ion in FAB (Fast Atom Bombardment) mass spectography, providing a key confirmation of the polymer length. Further, COSY-NMR (two-dimensional correlated spectroscopy) of the deprotected and purified polymer provides information on the ratio of the different base-pairing moieties in the polymer as well as quantitative information on the ratio of binding polymer to any solubilizing or other type moiety which may have been linked thereto.

Mobilities on ion exchange columns also provide information on the number of C+A base-pairing moieties in a polymer when purification is carried out at pH 2.5 and information on the number of G+U (or T) residues when the purification is run at pH 11. Structural verification is easiest when the polymers have been assembled from oligomer blocks, such as in Example 12, since any failure sequences then differ more substantially from the full-length sequences.

H. Assessment of the Polymer/Target Binding Affinity

Assessment of a binding polymer's affinity for its target is carried out by preparing aqueous solutions of the target polynucleotide, the polymer molecules, and an equal-concentration mixture of the two. The solutions are heated to about 60° C., and then slowly cooled to room temperature. Unmixed target and polymer-containing solutions are placed in cuvettes in series in the reference beam of a double-beam spectrophotometer and the polymer/target mixture is placed in the sample beam. When the cuvettes are scanned from about 320 nm to 220 nm, pairing between the binding polymer and its target genetic sequence is indicated by a negative absorbance profile—generally with two minima, one around 275 nm and a broader one around 230 nm. The next step is to monitor the absorbance at the dominant minima (around 275 nm) as the temperature is slowly raised from room temperature to near 100° C. When absorbance is plotted as a function of temperature, there is observed a relatively sharp rise in absorbance over a narrow temperature range. The temperature at which there is a maximum rate of rise in the plot corresponds to the melting temperature (Tm) for that polymer/target duplex. Typically, Tm values will be in the region of 50° C. to 90° C., with Tm values being higher for longer polymers and for polymers having a greater proportion of 3-bonding base-pairs (e.g., G and C) relative to 2-bonding base-pairs (e.g., A and U). Interestingly, the Tm values of these polymer/target duplexes are essentially independent of the salt concentration in the suspending medium, in contrast to the case for normal genetic duplexes.

The following examples illustrate a variety of subunit synthetic schemes, polymer construction methods, and compositions made and used according to the invention. The examples are in no way intended to limit the scope of the invention.

EXAMPLE 1

Preparation of ribonucleosides and deoxyribonucleosides

The following nucleosides are obtained from Sigma Chemical Co. (St. Louis, Mo.): deoxyuridine, deoxyguanosine, thymidine, deoxyadenosine, deoxycytidine, 5-bromodeoxyuridine, deoxyinosine, 2,6-diamino-9-(2-deoxy-B-D-erythro-pentofuranosyl) 9H-purine (2,6-diaminopurine deoxyriboside), uridine, guanosine, 5-methyluridine, adenosine, cytidine, 5-bromouridine, inosine.

2,6-Diamino-9-(B-D-ribofuranosyl)-9-H-purine (2,6-diaminopurine riboside) is obtained from Pfaltz and Bauer, Inc., Division of Aceto Chemical Co., Inc. (Waterbury, Conn.).

The following nucleosides are prepared by the literature methods indicated:

1-(2-Deoxy-B-D-erythro-pentofuranosyl)-2-pyrimidinone (2-hydroxypyrimidine deoxyriboside) is prepared by the method of P. Kohler, E. Volz, U. Sequin, and C. Tarn in *Nucleic Acid Chemistry* (L. B. Townsend and R. S. Tipson, eds) John Wiley and Sons, Inc. (1976).

1-(2-Deoxy-B-D-erythro-pentofuranosyl)-4-methoxy-2-pyrimidinone is prepared by the following procedure:

1-(3',5'-Di-O-benzoyl-2-deoxy-B-D-erythro-pentofuranosyl)- 4-methylthio-2-pyrimidinone (prepared as in Cech is treated with 200 ml of 0.2M sodium methoxide solution. The resulting solution is allowed to stand overnight at room temperature. This solution is then neutralized with Dowex 50×8 (H+ form) and filtered; the residue is dissolved in water (100 ml) extracted with ether (2.50 ml) and the aqueous phase evaporated. The residue is an amorphous material which is used directly in succeeding reactions.

2-Amino-9-(2-deoxy-B-D-erythro-pentofuranosyl)- 1,9-dihydro-6H-purine-6-thione (deoxythioguanosine) is prepared by the procedure of Iwamoto.

1-beta-D-Ribofuranosyl)-2-pyrimidinone (2-hydroxypyrimidine riboside) is prepared by the procedure of Niedballa.

1-(2-Deoxy-B-D-ribofuranosyl)-4-methoxy-2-pyrimidinone (2-hydroxypyrimidine deoxyriboside) is prepared by the procedure of Wightman.

2-Amino-9-beta-D-ribofuranosyl)-1,6-dihydro-6H-purine- 6-thione (thioguanosine) is prepared by the procedure of Fox.

EXAMPLE 2

Preparation of Base-Protected Nucleotides

Dimethoxytrityl chloride, N-benzoyladenosine, N-benzoyl- 2'-deoxyadenosine, N-benzoylcytidine, N-benzoyl-2'-deoxycytidine and N-isobutyryl-2'-deoxyguanosine are obtained from Sigma Chemicals. 9-Fluorenylmethoxycarbonyl chloride (FMOC chloride), trimethylchlorosilane, isobutyric anhydride, 4-nitrobenzoyl chloride and all organic solvents for reactions and chromatography are obtained from Aldrich Chemical Co. (Milwaukee, Wis.). Silica Gel is obtained from EM Science (Cherry Hill, N.J.).

2.1 Guanosine

The N-2 9-fluorenylmethoxycarbonyl derivative is prepared by the procedure below which is general for the protection of nucleoside amino groups:

Guanosine (1 mmol) is suspended in pyridine (5 ml) and treated with trimethylchlorosilane (5 mmol). After the solution is stirred for 15 minutes 9-fluorenylmethoxycarbonyl chloride (5 mmol) is added and the solution maintained at room temperature for 3 hours. The reaction is cooled in an ice bath and water (1 ml) is added. After stirring for 5 minutes conc. ammonia (1 ml) is added and the reaction stirred for 15 minutes. The solution is evaporated to near dryness and the residue dissolved in chloroform (10 ml). This solution is washed with sodium bicarbonate solution (5 ml, 10%), dried over sodium sulfate and evaporated. The residue is coevaporated several times with toluene and the product chromatographed on silica gel using a gradient of methanol in methylene chloride (0– 50%).

N-Isobutyrylguanosine is prepared by the method of Letsinger.

N-2 Acetylguanosine is obtained by the method of Reese.

2.2 Deoxyguanosine

The N-2 9-fluorenylmethoxycarbonyl derivative is prepared by the method of Heikkla.

The N-2 acetyl derivative is obtained from Research Plus Inc., Bayonne, N.J.

2.3 Deoxyadenosine

The N-6 2-(4-nitrophenyl)-ethoxycarbonyl derivative is prepared by the method of Himmelsbach.

N-6 4-Nitrobenzoyl-2'-deoxyadenosine is prepared using the procedure above for FMOC-guanosine except that 4-nitrobenzoyl chloride is substituted for FMOC chloride.

The N-6 2-(phenylsulfonyl)-ethoxycarbonyl derivative is prepared by the procedure for FMOC guanosine except the 2-(phenylsulfonyl)-ethyl chloroformate (Balgobin) is used as the acylating agent and N-methylimidazole or pyridine is used as the solvent.

2.4 Adenosine

The N-6 2-(4-nitrophenyl)-ethoxycarbonyl derivative is prepared by the method of Himmelsbach.

N-6 4-Nitrobenzoyladenosine is prepared using the procedure above for FMOC-guanosine except that 4-nitrobenzoyl chloride is substituted for FMOC chloride.

The N-6 2-(phenylsulfonyl)-ethoxycarbonyl derivative is prepared by the procedure for FMOC guanosine except the 2-(phenylsulfonyl)-ethyl chloroformate (Balgobin) is used as the acylating agent and N-methylimidazole or pyridine is used as the solvent.

2.5 Deoxycytidine

The N-4 2-(4-nitrophenyl)-ethoxycarbonyl derivative is prepared by the method of Himmelsbach.

The N-6 2-(phenylsulfonyl)-ethoxycarbonyl derivative is prepared by the procedure for FMOC guanosine except the 2-(phenylsulfonyl)-ethyl chloroformate (Balgobin) is used as the acylating agent and N-methylimidazole or pyridine is used as the solvent.

2.6 Cytidine

The N-4 2-(4-nitrophenyl)-ethoxycarbonyl derivative is prepared by the method of Himmelsbacho The N-6 2-(phenylsulfonyl)-ethoxycarbonyl derivative is prepared by the procedure for FMOC guanosine except the 2-(phenylsulfonyl)-ethyl chloroformate (Balgobin) is used as the acylating agent and N-methylimidazole or pyridine is used as the solvent.

2.7 2,6-diaminopurineriboside

The N-2,N-6-bis(9-fluorenylmethoxycarbonyl) derivative of 2,6-diaminopurine riboside is prepared by the general procedure.

The N-2,N-6-bis(isobutyryl) derivative is prepared by the general procedure.

2.8 2,6-diaminopurine-2'-deoxyriboside

The bis N-2,N-6-(9-fluorenylmethoxycarbonyl) derivative of 2,6-diaminopurine-2'-deoxyriboside is prepared by the general procedure.

2.9 Thioguanosine

The N-2 9-fluorenylmethoxycarbonyl derivative of thioguanosine is prepared by the general procedure.

2.10 2'-Deoxythioguanosine

The N-2 9-fluorenylmethoxycarbonyl derivative of 2'-deoxythioguanosine is prepared by the general procedure.

EXAMPLE 3

Preparation of 5'-amino-2',5-dideoxyribonucleoside subunits (FIG. 2B, wherein R'=H)

Carbon tetrabromide, sodium azide, p-toluenesulfonyl chloride (tosyl chloride), triphenyl phosphine and 10% palladium on carbon are purchased from Aldrich Chem Co. Lithium azide is obtained from Kodak Laboratory and Specialty Chemicals.

3.1 General Method

The nucleosides employed in this example are thymidine, N6-benzoyl-2'-deoxyadenosine, N4-benzoyl-2'-deoxycytodine, and 2'-deoxyinosine, 2-hydroxy-pyrimidine- 2'-deoxyriboside and the N2–N6-bisisobutyryl derivative of 2,6-diamino purine-2'-deoxyriboside (see Example 1). The required dried nucleoside (1 mmol) is weighed into a reaction vessel containing triphenyl phosphine (1.01 mmol) and lithium azide (5 mmol). After the solids are suspended in DMF, carbon tetrabromide (1.0 mmol) is added to the vessel. The solution is stirred at room temperature for 24 h. After quenching the reaction with methanol, the solution is evaporated to dryness. The residue is chromatographed on silica gel eluting with methanol/chloroform mixtures to afford the desired 5'-azido- 2',5'-deoxynucleoside.

The 5'-azido nucleoside (1 mmol) is dissolved in 1:1 methanol/DMF. Hydrogenation in the presence of 10% palladium on carbon (catalytic amount) under a hydrogen atmosphere (35 psi) occurs over 10 h. The solution is filtered, 1 mmol of toluenesulfonic acid is added, and the solution evaporated under reduced pressure to afford a crude solid. The solid is used without further purification.

3.2 5'-Azidouridine derivative

The 5'-azido derivative of 5-bromo-2'-deoxy uridine is prepared via the method described above. The 5'-azido-5-bromo-2'-deoxyuridine (1 mmol) is treated with triphenyl phosphine (1.5 mmol) in pyridine at room temperature for 2 h. Concentrated ammonia (1 ml) is added to the reaction vessel. After 14 h the solvent is removed under vacuum. The residue is dissolved in chloroform/methanol containing one equivalent of p-toluene sulfonic acid, and this solution is added to hexanes. The 5'-amino- 5-bromo-2'-deoxyuridine precipitate is collected and dried.

3.5 5'-Azidoguanosine

An alternate preparation of 5'-amino-2',5'-dideoxyguanosine is to treat the protected 2'-deoxyguanosine (protected at either the N-2-phenylacetyl or the N-2-FMOC derivative) (1 mmol) with tosyl chloride (1.3 mmol) in pyridine at 0° C. overnight. The solution is evaporated to dryness and the residue is dissolved in chloroform. The resulting solution is washed twice with aqueous sodium bicarbonate and dried over sodium sulfate. The solvent is evaporated and the residue chromatographed on silica gel eluting with methanol/chloroform mixtures. The resulting tosylate (1 mmol) is treated with sodium azide (6 mmol) in DMF at 80°–100° C. for a few hours. The solvent is removed by rotovap and the residue is chromatographed on silica gel eluting with chloroform/methanol solvent mixtures. The azide is reduced to the desired amine using the catalytic hydrogenation procedure above.

Alternate protecting groups for the base nitrogens of 2'-deoxycytidine, 2'-deoxyadenosine, 2'-deoxyguanosine, and 2,6-diaminopurinedeoxyriboside are 2-(phenylsulfonyl)ethoxycarbonyl for 2'-deoxycytidine and 2'-deoxyadenosine and the use of the 9'-fluorenylmethoxycarbonyl (FMOC) to protect 2'-deoxyguanosine and 2,6-diaminopurine deoxyriboside, as in Example 2.

EXAMPLE 4

Preparation of
5'-methylamino-2,5'-dideoxyribonucleoside subunits
(FIG. 2B, where R'=methyl)

N-Benzylmethylamine, p-toluenesulfonic chloride, trimethylsilyl chloride benzoyl chloride, phenylacetyl chloride, palladium on carbon (10%), palladium hydroxide on carbon (10%), triphenylmethyl chloride, 4,4'-dimethoxytrityl chloride, bis-(4-nitrophenyl)carbonate and 2-(4'-nitrophenyl)ethanol were purchased from Aldrich Chemical Company.

The following transformations describe the introduction of the 5'-alkylamino moiety (here methyl is the alkyl group) and may be used for the nucleosides containing adenine, guanine, or thymine. The 5'-tosylnucleoside is made as per the procedure of Robins. To a pyridine solution of the required dried nucleoside (1 mmol) is added p-toluenesulfonyl chloride (1.25 mmol). The reaction solution is stirred overnight at room temperature. The pyridine solution is diluted with chloroform and the resulting solution washed with water, then dried over sodium sulfate. The solvent is evaporated and the residue purified by chromatography on silica gel eluting with methanol/chloroform/0.1% dimethylaniline mixtures. The tosylate is isolated by addition of a chloroform solution of the tosylate to hexanes/ether (large volume, 1/1) and collection of the precipitate. Alternatively the chloroform solution from the aqueous workup is evaporated and the residue is re-crystallized from the appropriate solvent.

The 5'-tosylated nucleoside from above is dissolved in N-benzylmethylamine for 2–4 days. This solution is added to hexanes/ether (1/1, large volume) and the precipitate collected. The solid is purified by column chromatography on silica gel using methanol/chloroform/ 0.1% dimethylaniline mixtures as the eluting solvent. The fractions from the chromatography are pooled and evaporated to dryness. A 1:3 methanol:chloroform solution of the residue is added to an excess of ether and the precipitate collected and dried.

The 5'-methylamine nucleoside from the previous paragraph is base protected where necessary, in the manner described by Ti (differing only in the workup of the product, as described below).

The nucleoside (1 mmol) is dissolved in pyridine and treated with trimethylsilyl chloride (5 mmol). After 15 minutes the appropriate acid chloride (benzoyl chloride for adenosine, phenylacetyl chloride for guanosine) (2–3 mmol) is added and the solution stirred for 2 h. The reaction vessel is cooled to 0° C., the reaction quenched with 1/1 water/pyridine. After 15 minutes the reaction solution is treated with conc. ammonia. The reaction vessel is allowed warm to room temperature over 45 minutes, then tile pot contents evaporated.

The crude product from the reaction is dissolved in 5% aqueous acetic acid. The aqueous solution is extracted with ether after which the pH is adjusted to 10 with sodium hydroxide and sodium carbonate. The product is extracted with chloroform and dried over sodium sulfate. The solvent is evaporated and residue chromatographed on silica gel employing methanol:chloroform: 0.2% triethylamine as the eluting solvent. The fractions containing the product are pooled and evaporated. One equivalent of p-toluenesulfonic acid as a chloroform solution is added to a 3:1 chloroform:methanol solution of the tertiary amine. The nucleoside is precipitated as a salt by addition of this solution to an excess of ether.

It is now necessary to convert the 5'-alkylamino moiety to a form suitable for subsequent coupling steps. The base protected, tertiary amine nucleoside, as the p-toluene sulfonic acid salt (1 mmol) is dissolved in 1:1 methanol:DMF. Palladium (II) hydroxide on carbon is added to the vessel and the solution is placed under a hydrogen atmosphere for 10–20 h. The catalyst is removed by filtration and the solvent evaporated to give the crude secondary amine salt.

The amine salt from the previous paragraph is evaporated from pyridine twice then suspended in pyridine. Trityl chloride (1.5 mmol) and triethylamine (3 mmol) are added to the solution. After 2 h at room temperature the solution is diluted with chloroform and the resulting solution washed with 5% aqueous sodium bicarbonate. After drying over sodium sulfate the solution is evaporated to dryness. The residue is chromatographed on silica gel eluting with methanol/chloroform/0.1% DMA mixtures. The fractions containing the product are pooled then evaporated. The residue is dissolved in a minimum of chloroform and the product precipitated from hexanes. The solid is collected and dried to afford the basic subunit for methyl carbamate synthesis.

The above sequence for preparation of 5'-alkylamino nucleosides cannot be used for cytosine-containing nucleosides. Described now is a scheme for the preparation of 5'-alkylamino cytosine nucleosides. The method is also viable for other nucleosides.

Initially the 5' free, 3' protected, base protected nucleosides are required. The procedure described is of general use. N4-Benzoyl-2'-deoxycytosine (see Example 1) (2 mmol) is evaporated from pyridine twice, then suspended in pyridine. To this solution is added dimethoxytrityl chloride (2.8 mmol), triethylamine (3.0 mmol) and N,N-dimethyl-4-aminopyridine (0.1 mmol). The solution is stirred for 2 h, then the reaction is quenched by the addition of methanol. The solution is diluted with chloroform, then washed with 5% aqueous acetic acid. The organic solution is further washed with water, the dried over sodium sulfate. The solution is concentrated and the residue chromatographed on silica eluting with methanol: chloroform:0.1% DMA mixtures. The proper fractions are pooled, evaporated and the resulting residue dissolved in a minimum volume of chloroform. The solution is added to hexanes and the precipitate collected and dried.

A dry solution of N4-benzoyl-5'-dimethoxytrityl-2'-deoxycytosine (1 mmol) in anhydrous DMF is treated with p-nitrophenethyl-p-nitrophenylcarbonate (1.5 mmol) and N,N-dimethyl-4-aminopyridine (0.05 mmol) for 2 h. The solvent is carefully evaporated and the residue is dissolved in chloroform. The solution is washed successively with 5% aqueous acetic acid, water, 0.01N sodium hydroxide, and water. After drying the solution over sodium sulfate the solvent is evaporated and the residue taken on directly to the following transformation.

The cytosine nucleoside prepared in the preceding paragraph (1.0 mmol) is treated with 80% acetic acid in methanol for 2 h. The solvent is evaporated and the residue chromatographed on silica eluting with methanol:chloroform mixtures. Fractions containing the 5' free, 3' blocked nucleoside are pooled, evaporated and the resulting residue taken up in a minimum volume of methanol:chloroform. This solution is added to hexanes/toluene. The precipitate is collected and dried.

The 5'-alkylamino moiety is introduced as follows. The 3' protected, 5' free N4-benzoyloytidine (1 mmol) prepared in the preceding paragraph is dissolved in DMSO and treated with N,N'-dicyclohexylcarbodiimide and a trace of dichloroacetic acid. After 2 h the solution is filtered and the solid washed with acetonitrile. The filtrate and washings are combined and this solution is treated N-benzylmethylamine (5 mmol). After 5 minutes sodium cyanoborohydride (3 mmol) is added to the reaction flask. The pH is adjusted to 4–5 by addition of drops of glacial acetic acid to the solution. After standing overnight the solution is filtered, diluted with chloroform then extracted with dilute aqueous acetic acid. The aqueous extracts are combined and washed with chloroform. The pH of the aqueous solution is adjusted to 10 with sodium hydroxide and sodium carbonate. The aqueous solution is extracted with chloroform. The extracts are combined and dried over sodium sulfate. The solvent is evaporated and the residue chromatographed on silica gel eluting with methanol/chloroform/0.2% triethylamine mixtures. The fractions containing the product are combined and evaporated to dryness. The residue is dissolved in a minimum of chloroform, treated with on equivalent of p-toluenesulfonic acid, and the resulting solution added to ether. The solid is collected and dried to afford the 5' amine product.

The 4-nitrophenethylcarbonate protecting group at 3' is removed by treating the nucleoside with DBU in an aprotic solvent. An aqueous workup followed by chromatography as described for the previous intermediate affords the 3'-hydroxy nucleoside. The removal of the benzyl group and subsequent tritylation of the secondary 5' amine follow from the work described for the 5' methyl amino nucleosides above.

An alternative to the use of N-benzylmethylamine in the reductive amination step is to employ methyl amine. The secondary amine formed in that reaction is not purified but taken on in the same manner as the product of the debenzylation step above. The 3' hydroxyl would be freed after tritylation. A second alternative for the above oxidation step is to employ pyridine sulfur trioxide complex as the activating reagent in the oxidation of the 5' alcohol.

The reagent for protecting the 3'-hydroxyl group, p-nitrophenethyl-p-nitrophenyl carbonate, is prepared as follows. The mixed carbonate p-nitrophenethyl-p-nitrophenyl carbonate is prepared as follows. To a solution of p-nitrophenethylalcohol (10 mmol) in DMF is added bis-(__-nitrophenyl)carbonate (15 mmol) and triethylamine (15 mmol). The solution is stirred for 2 h, then 2 ml of water is added and stirring continued for 1 h. The solvent is evaporated and the resulting residue is chromatographed on silica eluting with methanol/chloroform mixtures. The fractions containing the mixed carbonate are pooled and evaporated. The residue is dissolved in chloroform, washed with aqueous NaOH, dried over sodium sulfate, and dried. A solution of the residue in a minimal volume of chloroform is added to hexanes and the resulting precipitated product collected and dried.

EXAMPLE 5

Preparation of morpholino-type subunits derived from ribonucleosides (the structure shown in FIG. 2C having protected morpholino nitrogen)

Ammonium biborate, sodium m-periodate, sodium cyanoborohydride, uridine, N4-benzoyl cytidine, and N6-benzoyl adenosine are obtained from Sigma Chemical Co. N2-isobutyryl guanosine is prepared as described in Example 2. Bis(p-nitrophenyl)carbonate is obtained from Aldrich Chemical Co. Benzylamine, and benzhydralamine can be obtained from Phlatz & Bauer, Inc.

Procedure 1. A typical synthesis is as follows: 4.2 grams of N4-benzoylated cytidine, prepared as per Watanabe, and 3.5 g of $(NH_4)_2B_4O_7$–4 $H_2O$ is added to 250 ml of methanol, the flask is capped and stirred in a warm water bath for 5 minutes. 2.8 g of $NaIO_4$ is added and the preparation stirred rapidly at room temperature for 90 minutes. This suspension is filtered and 0.75 g of $NaCNBH_3$ added to the filtrate. After 40 minutes at room temperature 5 g of trimethylacetic acid is added and the preparation dried under reduced pressure.

The solid is suspended in 100 ml of DMF and rotated under reduced pressure for 30 minutes in a room temperature water bath to remove any residual methanol. Next, 15 ml of triethylamine is added followed by 9.5 g of tritylchloride added slowly with rapid stirring. After 1 hr. the DMF is dried under high vacuum. The residue is suspended in 200 ml of chloroform and the insoluble material filtered off and discarded.

The final product (the structure shown in FIG. 2C wherein P is N4-benzoylated cytosine and the morpholino nitrogen is protected with a trityl group) can be isolated by silica gel chromatography wherein loading and washing is with chloroform and elution is with a chloroform/ethylacetate mix (typically 5:1 by vol.). Alternatively, hexane can be slowly added to the crude chloroform mixture to effect crystallization of the product and that product further purified by recrystallization from methanol. Similar methods, differing somewhat only in the purification conditions, can be used for preparation of the other ribonucleoside-derived morpholino-type subunits.

The morpholino subunits can also be prepared in good yield by suspending the base-protected ribonucleoside in a methanolic mixture of both the periodate and cyanoborohydride in the presence of a suitably-protected primary amine. The selection criteria for the amine protective group are: a) the protective group must not deactivate the amine to such an extent that the amine cannot react with the ribose-derived dialdehyde in the presence of cyanoborohydride; b) after closure of the morpholino ring the protected nitrogen must not be acylated under conditions required for subunit activation (see Examples 9, 10, & 11); and, c) the protective group must be readily cleavable when desired—such as by catalytic hydrogenation or by acid. Protected amines which satisfy these criteria are arylmethylamines such as benzylamine, benzhydrylamine and related substances. Morpholino-type subunits can be prepared by this method as follows.

Suspend 1.0 mmol of base-protected (where necessary) ribonucleoside in 250 ml of methanol, add 1.1 mmol of sodium periodate, 2 mmol of sodium cyanoborohydride, and then 1.2 mmol of one of the protected amines described above. After stirring 2 hours at room temperature the reaction mixture is dried under reduced pressure and the final product (the structure shown in FIG. 2C the morpholino nitrogen is protected) is purified by silica gel chromatography or recrystallization from suitable solvents as described above.

EXAMPLE 6

Preparation of 5'-methylsulfonic acid derivatives of Morpholino subunits (FIG. 2E)

For the preparation of subunits having the structure shown in FIG. 2E the uracil morpholino subunit from Example 5 is used as starting material. The amino function is protected with a carbamate moiety (e.g., carbobenzyloxy by reaction with the p-nitrophenyl carbonate of benzyl alcohol). The 5'-alcohol unit is now oxidized in the same manner as in the preparation of the n-alkylcytosine carbamate series of type B in Example 4. The resultant aldehyde is treated with phenyl diphenylphosphinylmethane sulfonate (Fild). Subsequently, treatment with hydrogen in the presence of palladium in a polar solvent followed by alcoholic KOH in DMF, and retritylation with tritylchloride and triethylamine in DMF produces the N-protected uracil subunit of the structure shown in FIG. E.

EXAMPLE 7

Preparation of 5'-sulfonic acid derivatives of N-aminomorpholino subunits (FIG. 2F)

5'-Mercapto-5'-deoxy-2',3'-O-isopropylidene inosine (Hampton) is oxidized with potassium hydroxide/oxygen in dimethylformamide as outlined by Wallace. The ketal moiety is cleaved with 2% aqueous acetic acid at 100° C. The diol is oxidized with periodate as per the synthesis of the morpholino subunit shown in FIG. 2C (Example 5) however, in this case, the amine component in Example 5 is not included in the reaction mixture. The dialdehyde intermediate is instead reacted with trityl hydrazine in the presence of sodium cyanoborohydride to yield the N-protected subunit of structure F of FIG. 2 wherein P is hypoxanthine.

EXAMPLE 8

Activation and Coupling of Ketal-type Subunits (The Linkage Shown in FIG. 5A)

8.1 Preparation of the Linking Agent

4-Methoxy-1,1-dioxo-5,6-dihydro-(2H)-Thiopyran is prepared from the available tetrahydrothiopyran-4-one (Aldrich) by ketalization with trimethyl orthoformate in methanol containing catalytic sulfuric acid, followed by oxidation with excess m-chlorolperbenzoic acid in methylene chloride, followed by acid promoted elimination of methanol using, for instance, methanesulfonic acid in hot chloroform (to drive off by-product methanol by distillation).

8.2 Preparation of Activated Monomers

5'-O-Dimethoxytritylthymidine is reacted with excess linking agent (previous paragraph) in hot tetrahydrofuran or DMF containing one equivalent of mercuric acetate (or trifluoroacetate). The mercury is removed using sodium trithiocarbonate containing NaOH. Alternatively, sodium borohydride may be used. Methanol is removed from the ketal using an aluminum chloride/triethylamine (1:2) complex in ether at 20° C. After complete exchange the product is purified by chromatography on silica gel using 1–10% methanol in chloroform.

8.3 Preparation of the Internucleoside Linkage

3'-O-Acetoxythymidine (or support bound oligomer with a 5' free hydroxyl) is reacted with excess activated monomer (from the previous paragraph) in $CH_3CN$ (or $CH_2Cl_2$, or THF, or DMF or other suitable solvent) in the presence of at least one equivalent of mercuric acetate. Mercury is removed by treatment with sodium trithiocarbonate at minus 20° C. in methanol/water containing sodium hydroxide. Alternatively, sodium hydroxide may be used.

EXAMPLE 9

Activation of N1-protected subunits where N2 is a hydroxyl (FIGS. 2 Band 2C)

To 18 ml of acetone (or DMF) add 1.38 g of morpholino N-tritylated, N4 benzoylated cytidine derivative (the structure shown in FIG. 2B or 2C) and 1.8 g of bis(p-nitrophenyl) carbonate followed by 1.8 ml of triethylamine. Cap and stir until dissolution is complete (about 15 minutes when acetone is the solvent, faster for DMF) and then incubate at 30° C. for 3 hours. Rotovap off the acetone, suspend in chloroform, and purify by silica gel chromatography developed with chloroform, containing a trace of N,N-dimethylaniline and 0 to 10% ethyl acetate.

EXAMPLE 10

Activation of N1-protected subunits where N2 is an amine (the structure shown in FIG. 2D)

Activation of a backbone-protected subunit having an amino N2 moiety (structure D of FIG. 2) is effected by first reacting 1.2 mmol of sulfuryl chloride with 5 mmol of triazole. Then without purification, this preparation is added to 1 mmol of the base-protected, backbone-protected subunit to give an activated urea. The reactivity of this active urea is on a par with the active carbonates prepared as in Example 9. It can be purified by silica gel chromatography in much the same manner as the active carbonates.

EXAMPLE 11

Activation of N1-protected subunits where E is a sulfonic acid (FIGS. 2E and 2F).

Subunits prepared as in Example 6 and 7 can be activated as follows. 1.0 mmol of base-protected (where necessary), backbone-protected subunit is suspended in 50 ml of DMF containing 2.5 mmol of dicyclohexylcarbodimide. After 10 min 5 mmol of triazole is added and the material stirred at room temperature for 30 min. DMF is removed under high vacuum and the activated product purified by silica gel chromatography.

EXAMPLE 12

Block Assembly in Solution of a Binding Polymer of the Sequence 5'-ACGUACGU a) Coupling Procedure Deprotect 2 mmol portions of both morpholino A subunit and morpholino G subunit prepared as in Example 5. This is accomplished by suspending 2 mmol of subunit in 100 ml of trifluoroethanol and adding 1 ml of trifluoroacetic acid. After 1 min add 10 ml of methanol and rotovap dry. Activate 2.2 mmol portions of morpholino C subunit and morpholino U subunit by the method described in Example 9.

Suspend the above deprotected A preparation in 20 ml of DMF, add 2 ml of triethylamine, and then add the above activated C preparation. Likewise, suspend the above deprotected G preparation in 30 ml of DMF, add 2 ml of triethylamine, and then add the above activated U preparation. Incubate both coupling reactions at 30° C. for 2 hrs. The two dimer products, 5'-AC and 5'-GU, are purified by silica gel chromatography developed with chloroform containing 1% to 5% methanol.

The 5'-AC dimer is deprotected essentially as above and the 5'-GU dimer is activated by the method described in Example 9, wherein the solvent used for the activation step is DMF. Coupling of these two dimer preparations is carried out as for the monomers above, except the coupling reaction is incubated at 30° C. for 5 hrs. The tetramer product, 5'-ACGU, is purified on a silica gel column developed with chloroform containing 2% to 8% methanol.

Forty-five percent of the tetramer preparation is deprotected as described above and the remaining 55% is activated as per the dimer above, and these two preparations are coupled as with the dimers above, excepting the reaction mixture is incubated overnight at 30° C. The resulting octomer, 5'-ACGUACGU, is purified on a silica gel column developed with chloroform 6 to 16% in methanol.

In related syntheses of polymers from subunits containing an acid-sensitive glycosidic linkage, (the structure shown in FIG. 2B), 80% acetic acid in methanol is used whenever cleavage of a p-methoxytrityl from the backbone is required for solution syntheses. Further, prior to rotovaping these deprotected preparations, one equivalent of p-toluenesulfonic acid is added to give the stable tosylate salt. For syntheses using subunits containing the structure shown in FIG. 2A backbone deprotection is done with 80% aqueous acetic acid (if solution phase), or 5% dichloroacetic acid in THF or acetonitrile (if solid-phase synthesis).

Excepting for differing methods of activation, as described in Examples 9, 10 and 11, the above methods for polymer assembly are general for subunit types of the structures shown in FIGS. 2B through 2F.

b) Configuring the Binding Polymer for a Solution Application

Twenty g of polyethylene glycol 1000 (average MW of 1000, Polysciences Inc.) is dissolved in 100 ml of DMF and 10 g of carbonyldiimidazole is added with stirring. After 40 min at room temperature 1.2 ml of water is added and stirring is continued for 20 min.

One half mmol of octomer from above is suspended in 100 ml of trifluorethanol and 1 ml of trifluoracetic acid added, or suspended in 80% acetic acid in methanol. After 1 min 10 ml of methanol is added and the solution dried under reduced pressure. Thereafter, the above activated polyethylene glycol solution is added to the backbone-deprotected octomer preparation, followed by 3 ml of diisopropylethylamine and 5 g of triazole. This mixture is stirred overnight at 30° C. The reaction mix is poured into ethyl acetate and the precipitated product collected by filtration or centrifugation.

c) Base-deprotection of the Derivatized Binding Polymer

The solid product is dried and then suspended in 100 ml of DMSO in a container capable of withstanding moderate pressure. Thereafter, 100 ml of concentrated ammonium hydroxide is layered carefully over the DMSO, the container tightly sealed, and then shaken to mix. This preparation is held at 30° C. overnight to effect complete deprotection of the bases. After the deprotection step the pressure is slowly released and then the preparation dried under aspirator vacuum to remove the ammonia. If the synthetic scheme has been such that the amine terminus of the polymer still carries a trityl-type protective group this is removed in the standard manner.

EXAMPLE 13

Solid-phase Assembly of a Binding Polymer of the Sequence 5'-GCAATGAAAGCT Targeted Against the tat Gene of the AIDS Virus 13.1 Preparation of Subunit with a 3'-O-Cleaveable Linker for Attachment to Solid Support for Stepwise Assembly of Oligomers Succinic anhydride, p-nitrophenol and dicyclohexylcarbodiimide are available from Aldrich Chemical Co.

The following demonstrates a general scheme applicable to the standard four nucleosides modified at the 5' position and protected where necessary as prepared in Example 4. N5'-methyl-N5'-tritylthymidine (1 mmol) is placed in flask with succinic anhydride (8 mmol). Acetonitrile then N-methylimidazole are added to the vessel. After 12h the solvent is evaporated and the residue chromatographed on silica gel, eluting initially with chloroform, then with 3–10% methanol/chloroform. The fractions containing the product were pooled and the solvent evaporated. The residue was dissolved in a minimum of chloroform and this chloroform solution was added to hexanes. The precipitate formed was collected and dried.

The subunit derivatized by the above method (1 mmol) was mixed with p-nitrophenol (8 mmol) in dioxane/pyridine (10/1). This solution was treated with dicyclohexylcarbodiimide (10 mmol) then stirred for 2h. The solution is filtered and the residue is washed with a small portion of DMF. This solution is used as is in the derivatization of solid supports.

13.2 Attachment of the First Subunit to the Support

Long-chain alkylamine control pore glass is available from Pierce Chemical Co.

The following demonstrates a general scheme applicable to the standard four nucleosides protected where necessary and carrying the succinoyl ether on the 3' oxygen, as prepared above. The control pore glass, derivatized with long chain alkylamine moieties (5 g of support with approximately 0.1 mmol of active sites/g of support), is washed with DMF containing 10% triethylamine then DMF. The solution of the succinoylated methyl amine thymidine subunit (1 mmol) is added to the column containing the control pore glass. The column is gently shaken to insure mixing of the solution through the support. After 2 days, the solution is removed by filtration and the support washed with acetonitrile. Underivatized amino groups are capped with a solution of p-nitrophenyl acetate and triethylamine in acetonitrile. After the support is washed with acetonitrile, then with 3/1 acetonitrile/DMF, the control pore glass containing the bound nucleoside is stored under acetonitrile.

13.3 Stepwise Assembly of the Oligomer Bound to a Solid Support

The following demonstrates the assembly of a support bound methyl carbamate-linked oligomer of the sequence (5') GCAATGAAAGCT (3'). These procedures can be used to synthesize any desired sequence by varying the order of addition of the individual subunits.

The support bound 5' tritylated methyl amino thymidine subunit (approximately 0.05 mmol of support bound thymidine), prepared above, is washed with methylene chloride. The support is treated with 2% dichloracetic acid in methylene chloride for 2 min to remove the trityl group. Washes of methylene chloride then 3/1 acetonitrile/DMF are passed through the support.

A solution of the cytosine-containing subunit prepared as in Example 4 and activated as in Example 9 (0.5 mmol), and diisopropylethylamine (1 mmol) in 3/1 acetonitrile/DMF are added to the support bearing the 5'-methylaminothymidine subunit. The funnel is gently rocked to mix the solution through the support. After 1–2h the solution is filtered and the support washed with 3/1 acetonitrile/DMF.

The support is again treated with 2% dichloroacetic acid in methylene chloride as detailed above. The succeeding nucleoside, blocked at the 5' terminus and bearing the p-nitrophenoxycarbonyl group at the 3' oxygen (prepared in Examples 4 and 9), is added to the support under the conditions described above. Subsequently, the subunits of G, A, A, A, G, T, A, A, C and G are added in order to the growing oligomer. The support bearing the oligomer is stored under acetonitrile.

13.4 Configuring the Binding Polymer for Attachment to a Solid Support for Diagnostic Application After addition of the final subunit the trityl moiety is cleaved in the standard manner and then 2 mmol of the p-nitrophenyl ester of N-trityl 6-aminocaproic acid is added and the support is gently shaken for 2 hrs.

13.5 Cleavage From the Support and Base Deprotection.

The support is thoroughly washed with DMF followed by acetonitrile and then dried under vacuum. The dry synthesis support is suspended in 15 ml DMSO and 15 ml of con $NH_4OH$ carefully layered over the DMSO. After tightly capping, the container is shaken overnight at 30° C. The following day pressure was slowly released, the slurry filtered, and the filtrate dried under high vacuum. The product is detritylated in the standard manner and then dried under reduced pressure.

EXAMPLE 14

Purification of the Binding Polymers

Fully-deprotected binding polymers prepared as in Examples 12 and 13 can be purified as illustrated below. Purification at pH 2.5 is general for binding polymers wherein about half or more of the base-pairing moieties are of the types shown in FIGS. 1(A), 1(B), and/or 1(C) Purification at pH 11 is general for binding polymers wherein about half or more of the base-pairing moieties are of the types shown in FIGS. 1(G), 1(H), 1(I), and/or 1(J).

14.1 Purification at pH 2.5

Water to be used for chromatography is degassed under aspirator vacuum and formic acid added to give pH 2.5 (solvent A). A corresponding pH 2.5 solution is made 2N in NaCl (solvent B). A third aqueous pH 2.5 solution is mixed 1:1 by volume with chromatographic-grade acetonitrile (solvent C).

Suspend fully-deprotected binding polymer, prepared as in Example 12 or 13 and containing about half or more of its base-pairing moieties of type 1, 2, and/or 3, in solvent A at a concentration of about 100 µg/ml. If the pH is higher than 2.5 adjust to pH 2.5 with formic acid. Load up to about 10 ml of this polymer solution on a chromatography column 1 cm in diameter and 10 to 20 cm in length which is packed with the cation-exchange support *S-Sepharose Fast Flow* (Pharmacia). Proportionately larger quantities can be loaded on larger columns of the same length—e.g., up to 60 ml can be loaded on a 2.5 cm diameter column and 250 ml on a 5 cm column. After washing the column thoroughly with solvent A elute with a linear gradient ranging from 100% solvent A to 100% solvent B and monitor the eluant at 254 nm. The desired binding polymer is generally the last and the largest peak to elute from the column. At least when the polymer is prepared by block assembly, base-line separations are often achieved. When peak shapes are unsymmetrical the problem generally has been due to insolubility of the binding polymer rather than lack of capacity of the chromatographic packing. Such a problem, which is most common when the binding polymers do not contain a solubilizing moiety, can often be solved by reducing the quantity of binding polymer loaded in a given run. When peaks are symmetrical but base-line separation is not achieved, substantial improvements are usually attained simply by eluting with a shallower gradient.

The eluant containing the polymer is desalted by loading on an equivalent-sized column packed with 35 micron chromatographic polypropylene (cat. no. 4342 from Polysciences, Inc.) and washing thoroughly with solvent A. If baseline separation was achieved in the foregoing cation exchange chromatography then pure product is obtained simply by eluting with solvent C; otherwise, the product is eluted with a linear gradient ranging from 100% solvent A to 100% solvent C. When the product is relatively acid-insensitive (i.e., composed of subunits of the types shown in FIG. 2C, 2D, 2E or 2F) the fractions containing the product are dried under reduced pressure. When the product is somewhat acid sensitive (i.e., composed of subunits of the types shown in FIGS. 2A or 2B) the solution is first neutralized with pyridine and then dried under reduced pressure.

14.2 Purification at pH 11

N,N-diethylethanolamine (Aldrich) is added to degassed water to adjust the pH to 11.0 (solvent D). A corresponding pH 11 solution 2 N in NaCl (solvent E) is prepared. A third pH 11 solution is mixed 1:1 by volume with chromatographic grade acetonitrile (solvent F).

Suspend fully-deprotected binding polymer, prepared as in Example 12 or 13 and containing about half or more of its base-pairing moieties of type 7, 8, 9, and/or 10, in solvent D at a concentration of about 100 µg/ml. If the pH is lower than 11 adjust to pH 11 with N,N-diethylethanolamine. Load up to about 10 ml of this polymer solution on a chromatography column 1 cm in diameter and 10 to 20 cm in length which is packed with anion-exchange support *Q-Sepharose Fast Flow* (Pharmacia). After washing the column thoroughly with solvent D elute with a linear gradient ranging from 100% solvent D to 100% solvent E and monitor the eluant at 254 nm.

The eluant containing the polymer is desalted by loading on an equivalent-sized column of polypropylene and washing thoroughly with solvent D. If baseline separation was achieved in the foregoing anion exchange chromatography then pure product is obtained simply by eluting with solvent F; otherwise, the product is eluted with a linear gradient ranging from 100% solvent D to 100% solvent F. Fractions containing the product are dried under reduced pressure.

While specific embodiments, methods, and uses of the invention have been described, it will be appreciated that various changes and modifications of the invention may be made without departing from the invention. In particular, although preferred polymer backbone structures have been described and illustrated, alternative cyclic and acyclic backbone structures described in the above-cited PCT patent application, Ser. No. US86/00544, and incorporated herein by reference, may also be suitable in soluble form for sequence-specific binding to single-stranded oligonucleotides.

It is claimed:

1. A method of producing a polymer composition effective to bind to a single-stranded polynucleotide containing a preselected target sequence of bases, comprising providing a subunit having one of the following structures:

2. The method of claim 1, which further includes coupling to a terminal region of the polymer molecules, a terminal moiety which is effective to enhance the solubility of the molecules in aqueous medium.

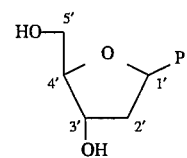

A.

-continued

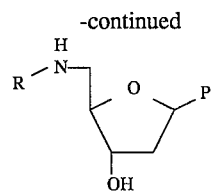 B.

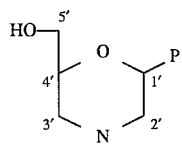 C.

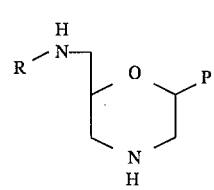 D.

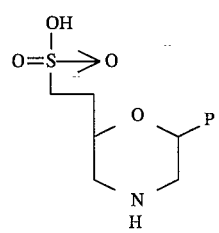 E.

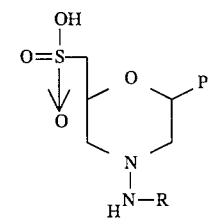 F.

where:

(i) P is a base-pairing moiety selected from the group consisting of purine and pyrimidine bases which are capable of binding by Watson/Crick pairing to contiguous, complementary bases in such target sequence, and (ii) R is H, an alkyl or a substituted alkyl group; and coupling the subunits to form heteromeric polymer molecules having one of the following corresponding structures, which show two of the subunits of the structure and an intersubunit linkage:

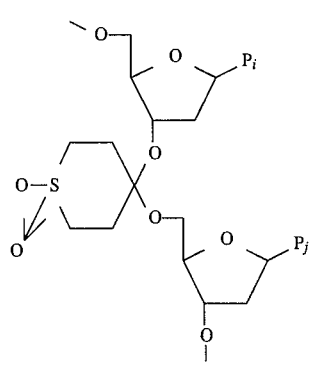 A-A

-continued

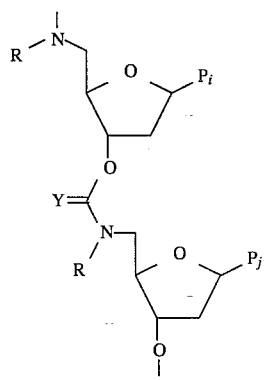 B-B

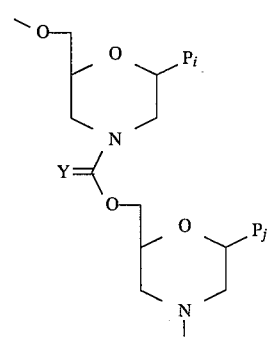 C-C

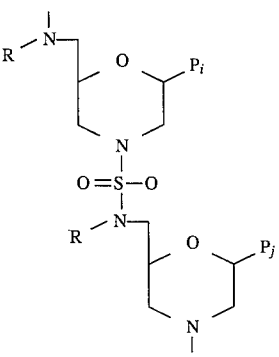 D-D

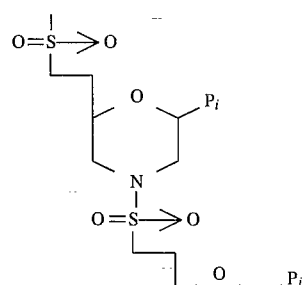 E-E

-continued

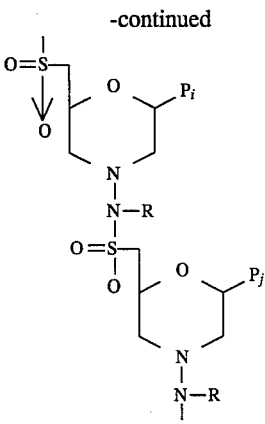

F-F where:

i) $P_1$ and $P_j$ are base-pairing moieties selected from the group consisting of purine and pyrimidine bases, which are capable of binding by Watson/Crick pairing to contiguous, complementary bases in the target sequence, (ii) the total number of base-pairing moieties in the polymer molecules is such that the moieties are effective to form at lease 12 hydrogen bonds with the complementary bases of the target sequence, and (iii) Y is an oxygen or sulfur atom.

* * * * *